(12) United States Patent
Cong et al.

(10) Patent No.: US 10,963,523 B2
(45) Date of Patent: Mar. 30, 2021

(54) CONSUMABLE DATA MANAGEMENT

(71) Applicant: Meso Scale Technologies, LLC., Rockville, MD (US)

(72) Inventors: Xinri Cong, Germantown, MD (US); Jerome Jackson, Phoenix, MD (US); Carl Stevens, Silver Spring, MD (US); Michael Vock, Loveland, OH (US); Jacob N. Wohlstadter, Potomac, MD (US)

(73) Assignee: Meso Scale Technologies, LLC., Rockville, MD (US)

( * ) Notice: Subject to any disclaimer, the term of this patent is extended or adjusted under 35 U.S.C. 154(b) by 0 days.

(21) Appl. No.: 16/052,711

(22) Filed: Aug. 2, 2018

(65) Prior Publication Data
US 2018/0341708 A1 Nov. 29, 2018

Related U.S. Application Data

(60) Continuation of application No. 15/583,370, filed on May 1, 2017, now Pat. No. 10,068,020, which is a
(Continued)

(51) Int. Cl.
*G06F 16/951* (2019.01)
*G06F 16/21* (2019.01)
(Continued)

(52) U.S. Cl.
CPC ....... *G06F 16/951* (2019.01); *G01N 35/0099* (2013.01); *G01N 35/00871* (2013.01);
(Continued)

(58) Field of Classification Search
None
See application file for complete search history.

(56) References Cited

U.S. PATENT DOCUMENTS 7,055,737 B1 * 6/2006 Tobin ................. G06Q 30/02
235/375
7,858,321 B2 12/2010 Glezer et al.
(Continued)

FOREIGN PATENT DOCUMENTS

CN 101720469 A 6/2010
EP 1 760 471 A2 3/2007
(Continued)

OTHER PUBLICATIONS

European Examination Report dated Apr. 10, 2019 received in European Patent Application No. 10 806 878.4.
(Continued)

*Primary Examiner* — Kristy A Haupt
(74) *Attorney, Agent, or Firm* — Scully, Scott, Murphy & Presser, P.C.

(57) ABSTRACT

The present invention relates to methods, devices and systems for associating consumable data with an assay consumable used in a biological assay. Provided are assay systems and associated consumables, wherein the assay system adjusts one or more steps of an assay protocol based on consumable data specific for that consumable. Various types of consumable data are described, as well as methods of using such information in the conduct of an assay by an assay system.

40 Claims, 4 Drawing Sheets

Related U.S. Application Data continuation of application No. 14/283,689, filed on May 21, 2014, now Pat. No. 9,659,096, which is a division of application No. 13/191,000, filed on Jul. 26, 2011, now Pat. No. 8,770,471.

(60) Provisional application No. 61/462,024, filed on Jan. 27, 2011, provisional application No. 61/400,441, filed on Jul. 27, 2010.

(51) Int. Cl.
| | | |
|---|---|---|
| G06Q 10/10 | (2012.01) | |
| G06Q 10/06 | (2012.01) | |
| G06Q 30/02 | (2012.01) | |
| G06Q 30/06 | (2012.01) | |
| G16H 10/40 | (2018.01) | |
| G07C 9/27 | (2020.01) | |
| G01N 35/00 | (2006.01) | |
| G01N 35/04 | (2006.01) | |
| G01N 35/10 | (2006.01) | |
| G06F 19/00 | (2018.01) | |
| G16B 50/00 | (2019.01) | |

(52) U.S. Cl.
CPC ......... *G01N 35/04* (2013.01); *G01N 35/1002* (2013.01); *G06F 16/21* (2019.01); *G06F 19/00* (2013.01); *G06Q 10/06* (2013.01); *G06Q 10/10* (2013.01); *G06Q 30/0201* (2013.01); *G06Q 30/0625* (2013.01); *G07C 9/27* (2020.01); *G16H 10/40* (2018.01); *G01N 2035/00881* (2013.01); *G01N 2035/0425* (2013.01); *G01N 2035/0475* (2013.01); *G16B 50/00* (2019.02)

(56) References Cited

U.S. PATENT DOCUMENTS

| | | | |
|---|---|---|---|
| 8,770,471 | B2 | 7/2014 | Cong et al. |
| 9,659,096 | B2 | 5/2017 | Cong et al. |
| 10,068,020 | B2* | 9/2018 | Cong ................ G06Q 30/0201 |
| 2002/0078011 | A1 | 6/2002 | Lee et al. |
| 2002/0078016 | A1 | 6/2002 | Lium et al. |
| 2003/0113713 | A1 | 6/2003 | Glezer et al. |
| 2004/0022677 | A1 | 2/2004 | Wohlstadter et al. |
| 2004/0189311 | A1 | 9/2004 | Glezer et al. |
| 2004/0220897 | A1 | 11/2004 | Bernhart et al. |
| 2005/0009122 | A1 | 1/2005 | Whelan et al. |
| 2005/0159982 | A1 | 7/2005 | Showalter et al. |
| 2005/0205673 | A1 | 9/2005 | Morris et al. |
| 2005/0210435 | A1 | 9/2005 | Zorrilla et al. |
| 2005/0240352 | A1 | 10/2005 | Liang |
| 2006/0199196 | A1 | 9/2006 | O'Banion et al. |
| 2006/0210435 | A1* | 9/2006 | Alavie ................ G01N 21/253 |
| | | | 422/65 |
| 2006/0216203 | A1 | 9/2006 | Fuller et al. |
| 2007/0004030 | A1 | 1/2007 | Ogura et al. |
| 2008/0024301 | A1 | 1/2008 | Fritchie et al. |
| 2008/0189163 | A1 | 8/2008 | Rosenberg et al. |
| 2008/0238627 | A1 | 10/2008 | Oldham et al. |
| 2008/0284602 | A1 | 11/2008 | Morris et al. |
| 2009/0066507 | A1 | 3/2009 | Lewington et al. |
| 2009/0269242 | A1 | 10/2009 | Nozawa |
| 2011/0022331 | A1 | 1/2011 | Clinton et al. |
| 2012/0145778 | A1 | 6/2012 | Cong et al. |
| 2014/0252088 | A1 | 9/2014 | Cong et al. |
| 2017/0235832 | A1 | 8/2017 | Cong et al. |

FOREIGN PATENT DOCUMENTS

| | | |
|---|---|---|
| EP | 1 767 948 A2 | 3/2007 |
| JP | 2003-216846 A | 7/2003 |
| JP | 2007-71554 A | 3/2007 |
| JP | 2007-148876 A | 6/2007 |
| JP | 2008-532048 A | 8/2008 |
| JP | 2009-2952 A | 1/2009 |
| JP | 2013-521901 A | 6/2013 |
| WO | 99/08090 A1 | 2/1999 |
| WO | 2006/060125 A2 | 6/2006 |
| WO | 2006/094388 A1 | 9/2006 |
| WO | 2009/006523 A2 | 1/2009 |
| WO | 2011/017082 A2 | 2/2011 |

OTHER PUBLICATIONS

Extended Supplementary European Search Report dated Apr. 4, 2016 received in European Patent Application No. 11 81 3039.2.
European Office Action dated Apr. 17, 2018 received in European Patent Application No. 11 813 039.2.
Japanese Notice of Reasons for Rejection dated Nov. 14, 2017 received in Japanese Patent Application No. 2016-192628, together with an English-language translation.
Japanese Notice of Reasons for Rejection dated Aug. 29, 2017 received in Japanese Patent Application No. 2013-521901, together with an English-language translation.
Japanese Decision of Rejection dated May 31, 2016 received in Japanese Patent Application No. 2013-521901, together with an English-language translation.
Japanese Notice of Reasons for Rejection dated Jun. 30, 2015 received in Japanese Patent Application No. 2013-521901, together with an English-language translation.
Canadian Examiner's Report dated Jul. 4, 2018 received in Canadian Patent Application No. 2,807,807.
Chinese Office Action dated Nov. 23, 2016 received in Chinese Patent Application No. 201180046586.X, together with an English-language translation.
Chinese Office Action dated Jun. 3, 2015 received in Chinese Patent Application No. 201180046586.X, together with an English-language translation.
U.S. Final Office Action dated Dec. 11, 2017 received in U.S. Appl. No. 15/583,370.
U.S. Office Action dated May 30, 2017 received in U.S. Appl. No. 15/583,370.
U.S. Final Office Action dated Aug. 16, 2016 received in U.S. Appl. No. 14/283,689.
U.S. Office Action dated Dec. 22, 2015 received in U.S. Appl. No. 14/283,689.
U.S. Office Action dated Jun. 22, 2015 received in U.S. Appl. No. 14/283,689.
U.S. Office Action dated Jul. 18, 2013 received in U.S. Appl. No. 13/191,000.
Japanese Notice of Reasons for Rejection dated Oct. 16, 2018 received in Japanese Patent Application No. 2016-192628, together with an English-language translation.
Japanese Decision of Rejection dated Jun. 4, 2019 received in Japanese Patent Application No. 2016-192628, together with an English-language translation.
Canadian Examination Search Report dated Sep. 11, 2019 received in Canadian Application No. 2,807,807.
Australian Examination Report dated Mar. 4, 2020 received in Australian Application No. 2019200316.
European Decision to Refuse dated Dec. 20, 2019 received in European Application No. 11 813 039.2.
European Minutes dated Dec. 18, 2019 received in European Application No. 11 813 039.2.
European Extended Search Report dated Apr. 7, 2020 received in European Patent Application No. 20 16 0064.0.
Canadian Examination Report dated Sep. 8, 2020 received in Canadian Application No. 2,807,807.
Japanese Notification of Reasons for Rejection dated Jan. 5, 2021 received in Japanese Patent No. 2019-181815, together with an English-language translation.
Australian Examination Report dated Jan. 22, 2021 received in Australian Application No. 2019200316.

* cited by examiner

CONSUMABLE DATA MANAGEMENT

CROSS-REFERENCE TO RELATED APPLICATIONS

This application is a continuation of copending U.S. patent application Ser. No. 15/583,370, filed May 1, 2017, which is a continuation of U.S. patent application Ser. No. 14/283,689, filed May 21, 2014, now U.S. Pat. No. 9,659,096, which is a divisional of U.S. patent application Ser. No. 13/191,000, filed Jul. 26, 2011, now U.S. Pat. No. 8,770,471, which claims the benefit of U.S. Provisional Application Ser. Nos. 61/462,024, filed Jan. 27, 2011 and 61/400,441, filed Jul. 27, 2010. The entire contents of each of these applications are incorporated herein by reference.

FIELD OF THE INVENTION

The present teaching relates to methods, devices and systems for associating consumable data with an assay consumable used in a biological assay.

BACKGROUND OF THE INVENTION

Numerous methods and systems have been developed for conducting assays. These methods and systems are essential in a variety of applications including medical diagnostics, veterinary testing, food and beverage testing, environmental monitoring, manufacturing quality control, drug discovery, and basic scientific research. During the manufacture and use of reagents and other consumables used in biological assays, the reagents and consumables are typically coded and labeled by the manufacturer in order to track them. In addition, a myriad of analytical parameters must be tracked in order to understand the analytical results of any given assay, often requiring input from various parallel tracking systems supplied by the manufacturer, customer or both.

SUMMARY OF THE INVENTION

The present invention provides an assay system configured to use an assay consumable in the conduct of an assay, the assay consumable comprising an assay consumable identifier and the assay system comprising: (a) a storage medium including a consumable data repository comprising local consumable data; and (b) a reader adapted to read consumable data from the consumable identifier, wherein the consumable data and local consumable data comprises (i) consumable identification and/or configuration information, and (ii) one or more steps of an assay protocol that can be applied by the system in the conduct of an assay using the consumable, wherein the system is configured to receive updates of the repository, the updates comprising additional consumable data and at least one consumable data type comprising:
  (x) one or more analytical tools that can be applied by the system to analyze data generated during and/or after the conduct of an assay,
  (y) assay system maintenance information,
  (z) system-consumable promotional information,
  (xx) system and/or consumable technical support information, or
  (yy) combinations thereof.

In one embodiment, the assay system of the invention includes an interface configured to send and/or receive consumable data to and/or from a vendor computing system.

The invention also provides a method of using an assay system configured to use an assay consumable in the conduct of an assay, the assay consumable comprising an assay consumable identifier and the assay system comprising: (a) a storage medium including a consumable data repository comprising local consumable data; and (b) a reader adapted to read consumable data from the consumable identifier, wherein the consumable data and local consumable data comprises (i) consumable identification and/or configuration information, and (ii) one or more steps of an assay protocol that can be applied by the system in the conduct of an assay using the consumable, wherein the system is configured to receive updates of the repository, the updates comprising additional consumable data and at least one consumable data type comprising (x) one or more analytical tools that can be applied by the system to analyze data generated during and/or after the conduct of an assay, (y) assay system maintenance information, (z) system-consumable promotional information, (xx) system and/or consumable technical support information, or (yy) combinations thereof, the method comprising the steps of:
  (a) reading consumable data from the consumable identifier;
  (b) adjusting one or more operations performed by the system before, during, and/or after the conduct of the assay by the system based on the consumable data;
  (c) conducting an assay in the assay system using the assay consumable; and
  (d) receiving the updates of the repository.

Moreover, also contemplated is a method of enabling use of an assay system by a system/consumable vendor, the assay system being configured to use an assay consumable in the conduct of an assay comprising an assay consumable identifier and the assay system comprising (a) a storage medium comprising local consumable data; and (b) a reader adapted to read consumable data from the consumable identifier, wherein the system/consumable vendor maintains a master consumable data repository comprising consumable data; the method comprising the step of providing consumable data to a customer from the master consumable data repository to enable use in the system of the consumable data.

Still further, the invention includes an assay system configured to use an assay consumable in the conduct of an assay, the assay consumable comprising an assay consumable identifier and the assay system comprising: (a) an interface configured to send and/or receive consumable data to and/or from a vendor computing system, (b) a storage medium comprising local consumable data, and (c) a reader adapted to read consumable data from the consumable identifier, wherein the consumable data comprises:
  (i) consumable identification and/or configuration information, and
  (ii) one or more steps of an assay protocol that can be applied by the system in the conduct of an assay using the consumable.

Another embodiment of the invention is a method of tracking use of assay consumables in an assay system, the assay consumable comprising an assay consumable identifier and the assay system comprising (a) an interface configured to send and/or receive consumable data to and/or from a vendor computing system, (b) a storage medium comprising local consumable data, and (c) a reader adapted to read information from the consumable identifier, wherein the consumable data and local consumable data comprises (i) consumable identification and/or configuration information, and (ii) one or more steps of an assay protocol that can be applied by the system in the conduct of an assay using the consumable, the method comprising the steps of:

(a) reading consumable data from the consumable identifier;

(b) configuring the assay system for use of the assay consumable in the conduct of an assay in the system using the consumable data;

(c) conducting an assay in the assay system using the assay consumable;

(d) storing system-consumable use information to the storage medium; and (e) sending system-consumable use information to the vendor computing system via the interface.

Also included is a method of controlling customer access to an assay system by a system vendor wherein the system comprises a system identifier, the method comprising the steps of:

(a) receiving the system identifier from a customer, wherein the system identifier is sent to a vendor computing system;

(b) identifying the system identifier by the vendor; and (c) performing one or more operations selected from:
 (i) enabling full access to the apparatus and/or a consumable used in the apparatus;
 (ii) enabling partial access to the apparatus and/or a consumable used in the apparatus; or
 (iii) denying access to the apparatus and/or a consumable used in the apparatus.

A further embodiment of the invention is a method of generating and maintaining consumable data and consumable data for a consumable comprising:

(a) manufacturing a consumable used in the conduct of an assay;

(b) generating a database comprising consumable data associated with the consumable, wherein the database comprises information used to associate the consumable data for the consumable; and (c) maintaining the database on a server.

Moreover, the invention includes a method of providing consumable data for a consumable to a customer comprising:

(a) receiving a query from the customer for consumable data associated with the consumable; and (b) sending consumable data for the consumable by a medium comprising email attachment, a compact disc, a memory card/stick, a flash drive, a web data storage service, or combinations thereof.

Still further, the invention provides a method of providing consumable data for a consumable to a customer comprising:

(a) receiving a query from a customer system via a direct interface for consumable data associated with the consumable, wherein the direct interface comprises an internet connection between the customer system and a vendor server; and (b) sending consumable data for the consumable via the interface to the customer system.

Also contemplated is a computer readable medium having stored thereon a computer program which, when executed by a computer system operatively connected to an assay system, causes the assay system to perform a method of conducting an assay on the assay system, wherein the assay system is configured to use an assay consumable in the conduct of the assay and the assay system comprises: (a) a storage medium including a consumable data repository comprising local consumable data; and (b) a reader adapted to read consumable data from the consumable identifier; the method comprising the steps of:

(a) reading consumable data from a consumable identifier associated with the assay consumable, wherein the consumable data and local consumable data comprises: (i) consumable identification and/or configuration information, and (ii) one or more steps of an assay protocol that can be applied by the system in the conduct of the assay using the consumable;

(b) adjusting one or more operations performed by the system before, during and/or after the conduct of the assay based on the consumable data;

(c) conducting the assay in the assay system using the assay consumable; and (d) receiving updates of the repository, the updates comprising additional consumable data and at least one consumable data type comprising (x) one or more analytical tools that can be applied by the system to analyze data generated during and/or after the conduct of an assay, (y) assay system maintenance information, (z) system-consumable promotional information, (xx) system and/or consumable technical support information, or (yy) combinations thereof.

In an additional embodiment, the invention provides a computer readable medium having stored thereon a computer program which, when executed by a computer system, causes the computer system to perform a method of enabling use of an assay system by a system/consumable vendor, the assay system being operatively connected to the computer system and configured to use an assay consumable in the conduct of an assay comprising an assay consumable identifier and the assay system comprising (a) a storage medium comprising local consumable data; and (b) a reader adapted to read consumable data from the consumable identifier, wherein the system/consumable vendor maintains a master consumable data repository comprising consumable data; the method comprising the step of receiving consumable data from the master consumable data repository to enable use of the consumable in the system.

In a specific embodiment, a computer readable medium is provided having stored thereon a computer program which, when executed by a computer system, causes the computer system to perform a method of tracking use of assay consumables in an assay system operatively connected to the computer system, the assay consumable comprising an assay consumable identifier and the assay system comprising: (a) an interface configured to send and/or receive consumable data to and/or from a vendor computing system, (b) a storage medium comprising local consumable data, and (c) a reader adapted to read information from the consumable identifier, the method comprising the steps of:

(a) reading consumable data from the consumable identifier, wherein the consumable data and local consumable data comprises (i) consumable identification and/or configuration information, and (ii) one or more steps of an assay protocol that can be applied by the system in the conduct of an assay using the consumable;

(b) configuring the assay system for use of the assay consumable in the conduct of an assay in the system using the consumable data;

(c) conducting an assay in the assay system using the assay consumable;

(d) storing system-consumable use information to the storage medium; and (e) sending system-consumable use information to the vendor computing system via the interface.

Additionally, the invention includes a computer readable medium having stored thereon a computer program which, when executed by a computer system, causes the computer system to perform a method of controlling customer access to an assay system by a system vendor wherein the system comprises a system identifier, the method comprising the steps of:

(a) receiving the system identifier from a customer, wherein the system identifier is sent to a vendor computing system;

(b) identifying the system identifier by the vendor; and (c) performing one or more operations selected from:
(i) enabling full access to the apparatus and/or a consumable used in the apparatus;
(ii) enabling partial access to the apparatus and/or a consumable used in the apparatus; or
(iii) denying access to the apparatus and/or a consumable used in the apparatus.

Still further, the invention includes a computer readable medium having stored thereon a computer program which, when executed by a computer system, causes the computer system to perform a method of generating and maintaining consumable data and consumable data for a consumable comprising:

(a) generating a database comprising consumable data associated with the consumable, wherein the database comprises information used to associate the consumable data with the consumable; and (b) maintaining the database on a server.

Also contemplated is a computer readable medium having stored thereon a computer program which, when executed by a computer system, causes the computer system to perform a method of providing consumable data for a consumable to a customer, the method comprising:

(a) receiving a query from the customer for consumable data associated with the consumable; and (b) sending consumable data for the consumable by a medium comprising email attachment, a compact disc, a memory card/stick, a flash drive, a web data storage service, or combinations thereof.

Moreover, the invention includes a computer readable medium having stored thereon a computer program which, when executed by a computer system, causes the computer system to perform a method of providing consumable data for a consumable to a customer, the method comprising:

(a) receiving a query from a customer system via a direct interface for consumable data associated with the consumable, wherein the direct interface comprises an internet connection between the customer system and a vendor server; and (b) sending consumable data for the consumable via the interface to the customer system.

In a preferred embodiment, the assay consumable comprises at least one assay test site for the assay, and preferably, the test site comprises a plurality of distinct assay domains, at least two of the domains comprising reagents for measuring different analytes. The test sites can be wells and/or chambers in the assay consumable. In one specific embodiment, the assay consumable comprises a plurality of wells and the consumable further includes at least one element comprising a plate top, plate bottom, working electrodes, counter electrodes, reference electrodes, dielectric materials, electrical connections, dried and/or liquid assay reagents, or combinations thereof. Alternatively or additionally, the assay consumable comprises a flow cell and the consumable can be a cartridge further comprising at least one element including one or more fluidic components, one or more detection components, one or more assay cells, reagents for carrying out an assay, working electrodes, counter electrodes, reference electrodes, dielectric materials, electrical connections, dried and/or liquid assay reagents, or combinations thereof. In this embodiment, the cartridge comprises at least one assay cell that includes a plurality of distinct assay domains, at least two of the domains comprising reagents for measuring different analytes. Still further, the assay consumable can be a container adapted to receive one or more assay reagents.

The invention provides systems, methods, and computer readable media configured to send, receive, and make use of consumable data associated with a consumable in an assay system. In one embodiment, the consumable data comprises information used to identify at least one element including (i) the assay consumable, (ii) one or more test sites within the consumable, (iii) a reagent and/or sample that has been or will be used in the consumable, or (iv) combinations thereof. Still further, the consumable data is used to distinguish a first test site within the consumable from a different test site within the consumable.

Additionally, consumable data can be consumable information comprising lot identification information, lot specific analysis parameters, manufacturing process information, raw materials information, expiration date, calibration data, threshold information, the location of individual assay reagents and/or samples within one or more test sites of the assay consumable, Material Safety Data Sheet (MSDS) information, or combinations thereof.

Still further, consumable data includes sample information comprising the location of samples within the at least one test sites of the assay consumable, assay results obtained on the assay consumable for the sample, identity of samples that have been and/or will be assayed in the assay consumable, or combinations thereof. In addition, consumable data also includes chain of custody information, including but not limited to information regarding the control, transfer, analysis of the sample, or combinations thereof. Moreover, chain of custody information also includes customer identification, time and date stamp for the assay, location of the assay system during the assay, calibration and QC status of the assay system during the assay, custody and/or location information for the assay consumable before and after the conduct of the assay, assay results for the sample; time, date, manufacturing personnel or processing parameters for one or more steps during the manufacture of the assay consumable; custody, location and or storage conditions for the assay consumable following manufacture and/or between steps during the manufacture of the assay consumable; or combinations thereof.

Still further, consumable data includes consumable/test site information comprising consumable type and structure, location and identity of assay reagents included with the assay consumable, location and identity of assay reagents within an assay test site of the assay consumable, or combinations thereof.

Also contemplated is consumable data that includes assay process information comprising assay parameters to be applied by the reader during the assay, a sequence of steps to be applied by the reader during the assay, the identity, concentration, and/or quantity of assay reagents to be used or added during the assay, the type or wavelength of light to be applied and/or measured by the reader during the assay, the temperature to be applied by the reader during the assay, an incubation time for the assay, statistical or analytical methods to be applied by the reader to raw data collected during the assay, or combinations thereof. In a specific embodiment, the assay conducted in the system is a multi-step assay and the assay process information relates to a step or step(s) of the multi-step assay. Therefore, consumable/test site information comprises information concerning assays previously performed by a reader on one or more test sites of the consumable; information concerning assays to be performed by an assay reader or a component thereof on one or more test sites within the consumable; or combinations thereof.

Moreover, consumable data also includes consumable security information comprising information concerning assay consumable authentication; information concerning appropriate placement and/or orientation of the assay consumable in the system; information concerning defects in the assay consumable and/or a test site thereof; or combinations thereof.

The consumable data can be used by the system to adjust the operation of at least one component of the assay system comprising one or more sensors; mechanisms to transport the assay consumables into and out of the system; mechanisms to align and orient the assay consumables with the one or more sensors and/or with electrical, mechanical or fluidic interfaces in the system; mechanisms, electronics or software to track and/or identify assay consumables; mechanisms to store, stack, move and/or distribute one or more consumables; or combinations thereof.

DETAILED DESCRIPTION OF VARIOUS EMBODIMENTS

Figure 1:
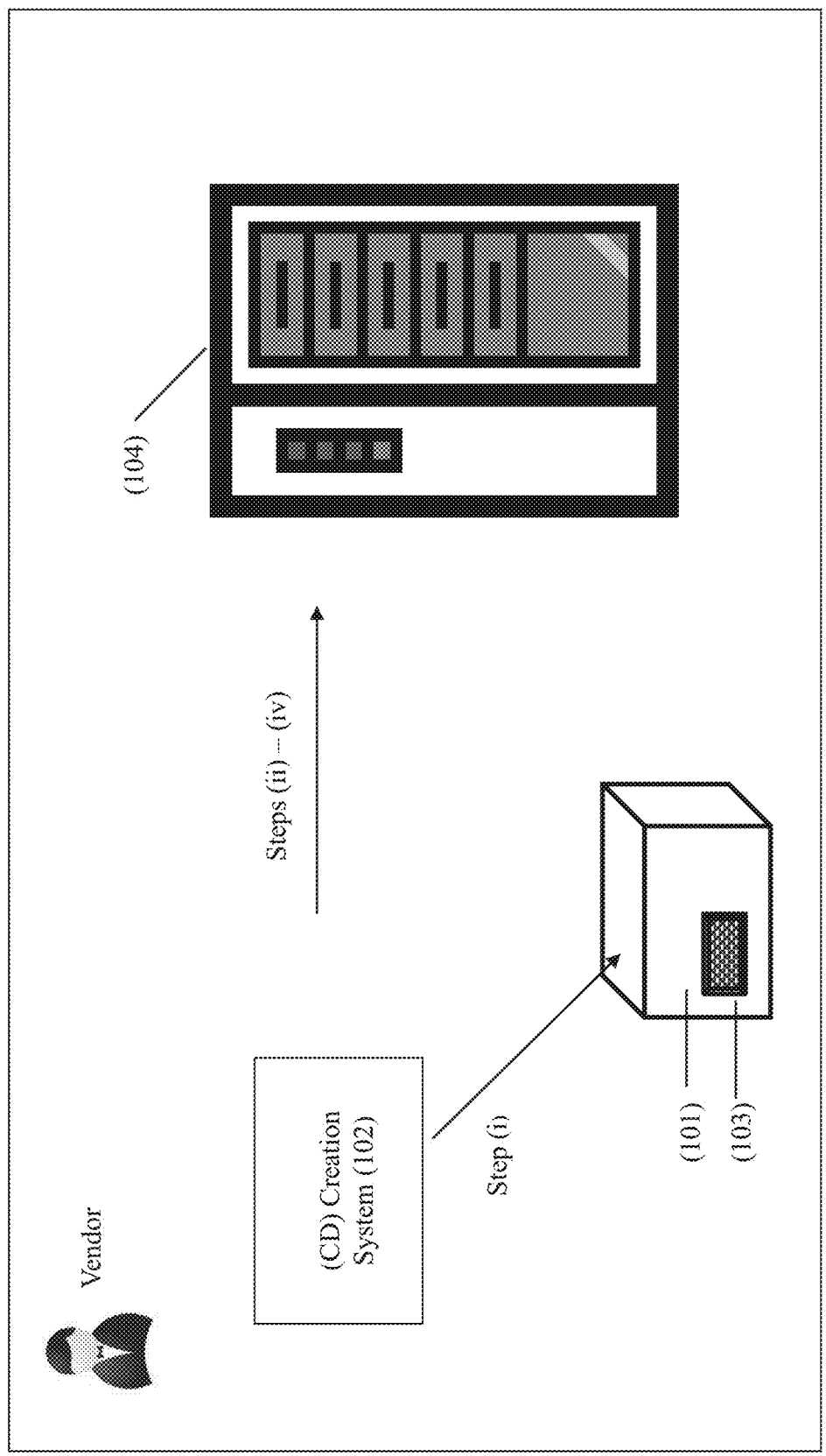
FIG. 1 illustrates the generation and storage of consumable data and consumable data by a consumable manufacturer.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The assay consumables and systems used in the present invention include a variety of devices and configurations. In one embodiment, the assay system used in the present invention includes an assay reader capable of conducting a biological assay using an assay consumable. The assay consumable comprises an identifier (referred to alternatively throughout the specification as an identifier, a consumable identifier, or an assay consumable identifier) and the assay system, reader or a component thereof comprises an identifier controller that interacts with the identifier. As described hereinbelow, the identifier includes information concerning the assay consumable, which cancan include but is not limited to, how the consumable is manufactured and handled prior to use and how the consumable is used in an assay system (referred to collectively as "consumable data"). Therefore, the assay system is configured to use an assay consumable in the conduct of an assay, and the assay system includes a reader adapted to (i) read information from an assay consumable identifier associated with the assay consumable; and optionally, (ii) erase information from the assay consumable identifier; and/or (iii) write information to the assay consumable identifier.

In a specific embodiment, the invention provides an assay system configured to use an assay consumable in the conduct of an assay, wherein the assay consumable includes an assay consumable identifier as described herein and the assay system includes (a) a storage medium comprising consumable data repository; and (b) a reader adapted to read information from the consumable identifier. In one embodiment, the system comprises a storage medium including a consumable data repository comprising local consumable data. The local consumable data stored to the assay system includes consumable identification and/or configuration information and one or more steps of an assay protocol that cancan be applied by the system in the conduct of an assay using a consumable. For example, the assay consumable identifier includes information that can be used to identify a specific consumable, e.g., lot specific information for a given lot of consumables and/or information that is specific to an individual consumable, and the corresponding local consumable data stored to the assay system includes information that is used to identify a consumable associated with the system, e.g., as a member of a given lot or as an individual consumable within a lot and it also includes information that is used by the system once the consumable is identified to carry out an assay protocol using that consumable. Still further, the consumable data (and/or local consumable data) can include one or more analytical tools that can be applied by the system to analyze data generated using that consumable, system and/or consumable technical support information or combinations thereof. Moreover, the system can also be configured to receive updates to the consumable data repository from a remote storage medium, wherein those updates include additional consumable data, including but not limited to additional consumable identification and/or configuration information, assay protocol information, and one or more of the following: (x) one or more analytical tools that can be applied by the system to analyze data generated during and/or after the conduct of an assay, (y) assay system maintenance information, (z) system-consumable promotional information, and (xx) system and/or consumable technical support information.

The use of the identifier/consumable data in the system is illustrated in FIGS. 1-4. FIG. 1 shows how consumable data is generated, stored and used by the manufacturer, distributor, or supplier (referred to herein as "vendor"). First, the vendor generates a consumable and/or a set or lot of consumables (101) and for that consumable or lot of consumables, consumable data is generated using a consumable data (CD) creation system (102) and stored to a consumable identifier (103) associated with the consumable or lot of consumables (step i). The consumable data is generated by the consumable vendor before, during and/or after the individual consumable and/or lot of consumables are made and/or distributed. The CD creation system generates a database of CD information for that consumable or lot, i.e., a CD database, to which consumable data is stored. The CD database is sent to a CD Server (104) which includes a master repository of all consumable data. In addition, the CD creation system stores information that is used to associate a given consumable identifier with consumable data in the master repository. The CD creation system and/or CD Server are located on a remote computing system, i.e., a computing system remote from the assay system and/or the customer or customer, e.g., a site maintained by the vendor. Therefore, as shown in FIG. 1, the vendor generates consumable data for a consumable or lot (a) and stores that information to a consumable identifier (b) associated with that consumable or lot. The CD system also (step ii) generates a CD database; (step iii) stores consumable data to the CD database; and (step iv) sends the CD database to the CD Server (c), which includes a master repository of all consumable data.

Figure 2:
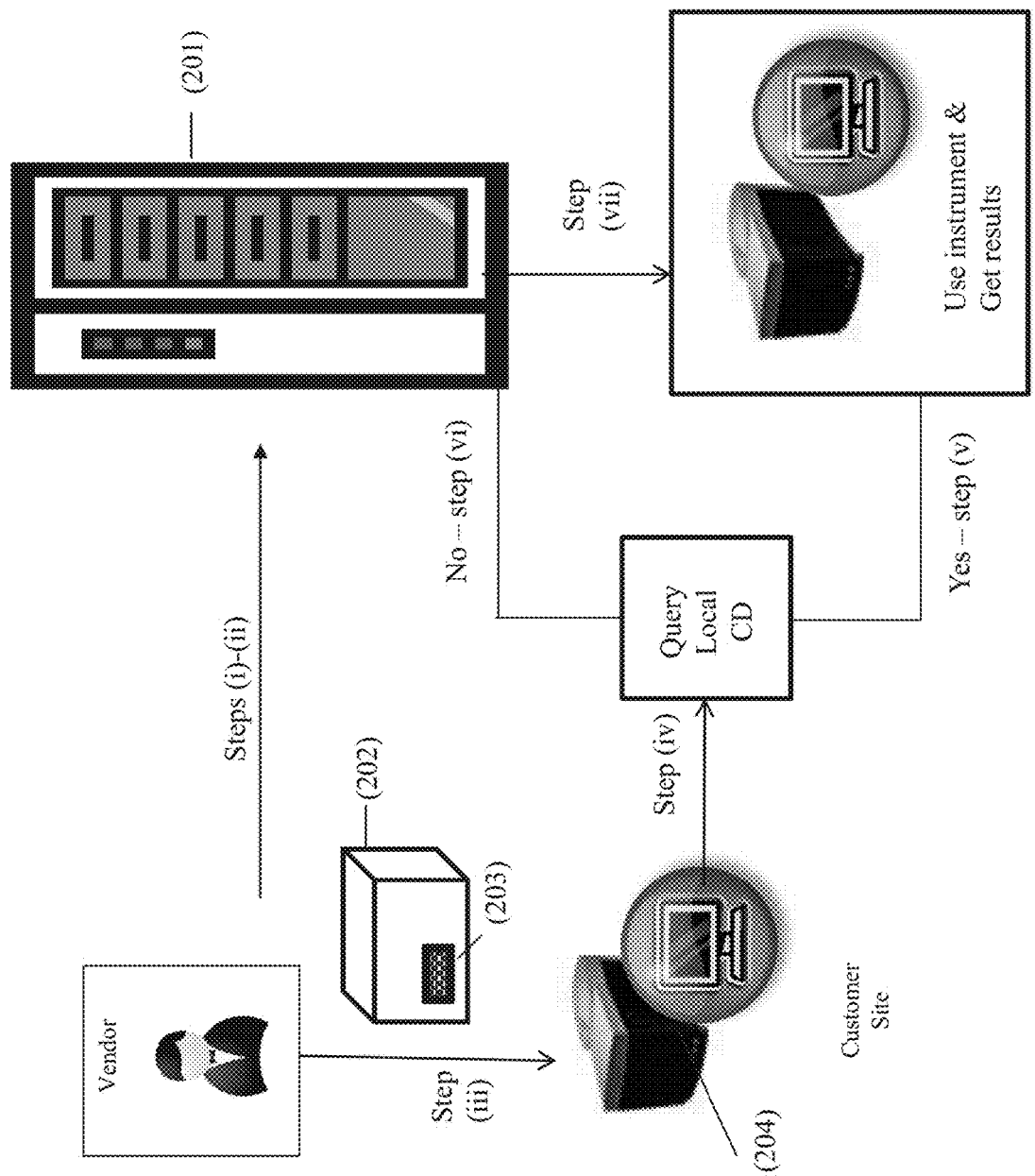
FIG. 2 illustrates the distribution of consumable data to a customer in response to a query for consumable data.

FIG. 2 illustrates one method of distributing consumable data to a customer or designated user of a customer (referred to collectively herein as a "customer"). Upon receipt of an order from a customer or when the consumable or lot is manufactured (step i), the vendor generates, stores and sends a CD database to the CD server (201) (step ii). The CD database can include order fulfillment information, i.e., a summary of the components of the order for a given customer so that the system can verify that all components of the order have been supplied to the customer. The customer receives the consumable (202), including consumable identifier (203), and contacts the consumable with the assay system (204) in preparation for the conduct of an assay (step iii), the system reads the information stored to the assay consumable identifier (203) and that information is used by the system to identify the consumable (202) (step iv). The system reviews the consumable data stored locally on the system in a local storage medium (referred to in FIG. 2 as "local CD") to identify that consumable data stored to the storage medium that can be used for the conduct of an assay using a given consumable. If the storage medium includes the consumable data for that consumable or lot, the consumables can be used in the system (step v). If the storage medium does not include consumable data for that particular consumable or lot of consumables, the system can query the customer for that consumable data and the customer can communicate with the vendor to receive the requisite consumable data, e.g., via email, compact diskette, memory card/stick, flash drive, web data storage service, etc. (step vi). The vendor sends consumable data binary files (including but not limited to encrypted XML files) to the customer, e.g., as an email attachment to a customer email account, the customer loads that file attachment to the assay system and the system software stores the consumable data to the local system consumable data repository. The consumable/lot of consumables can then be used in the instrument (step vii).

In an alternative embodiment, the CD server can be connected to the system via a direct interface which can automatically obtain the consumable data from the CD server if it is not available on the system locally. In this embodiment, the vendor generates, stores and sends a CD database to the CD server for a consumable order and/or lot of consumables, as shown in FIG. 2 and as described above. Thereafter the customer receives the consumable, order and/or lot and contacts the system with the consumable identifier to enable the system to identify the consumable or lot. The system software queries the system consumable data repository for the consumable data associated with that consumable identifier and if that consumable data is available locally on the system, the software will adjust the system based on the consumable data, if necessary. If the consumable data is not present in the system consumable data repository, the system will either (i) prompt the customer to manually obtain the consumable data from the vendor, or (ii) automatically, via a direct interface with the CD server, obtain the consumable data from the CD server and store that information locally on the system consumable data repository. Once the consumable data is available locally on the system, the software adjusts the system based on the consumable data, if necessary, and conducts an assay. Once the consumable data is available locally on the system, the consumable or lot can be used in the system to conduct an assay and display the assay results to the customer. In a specific embodiment, the system software adjusts the output to the customer based on the consumable data.

In addition, the CD server can periodically send consumable data for new lots of consumables/consumable types to a customer assay system, e.g., via email, CD, memory card/stick, flash drive and/or via a remote interface between the system and the CD server. The storage medium comprises a consumable data repository including the consumable data and the assay system is configured to receive updates to the repository from a remote storage medium, e.g., via email, CD, memory card/stick, flash drive and/or via a remote interface.

Figure 3:
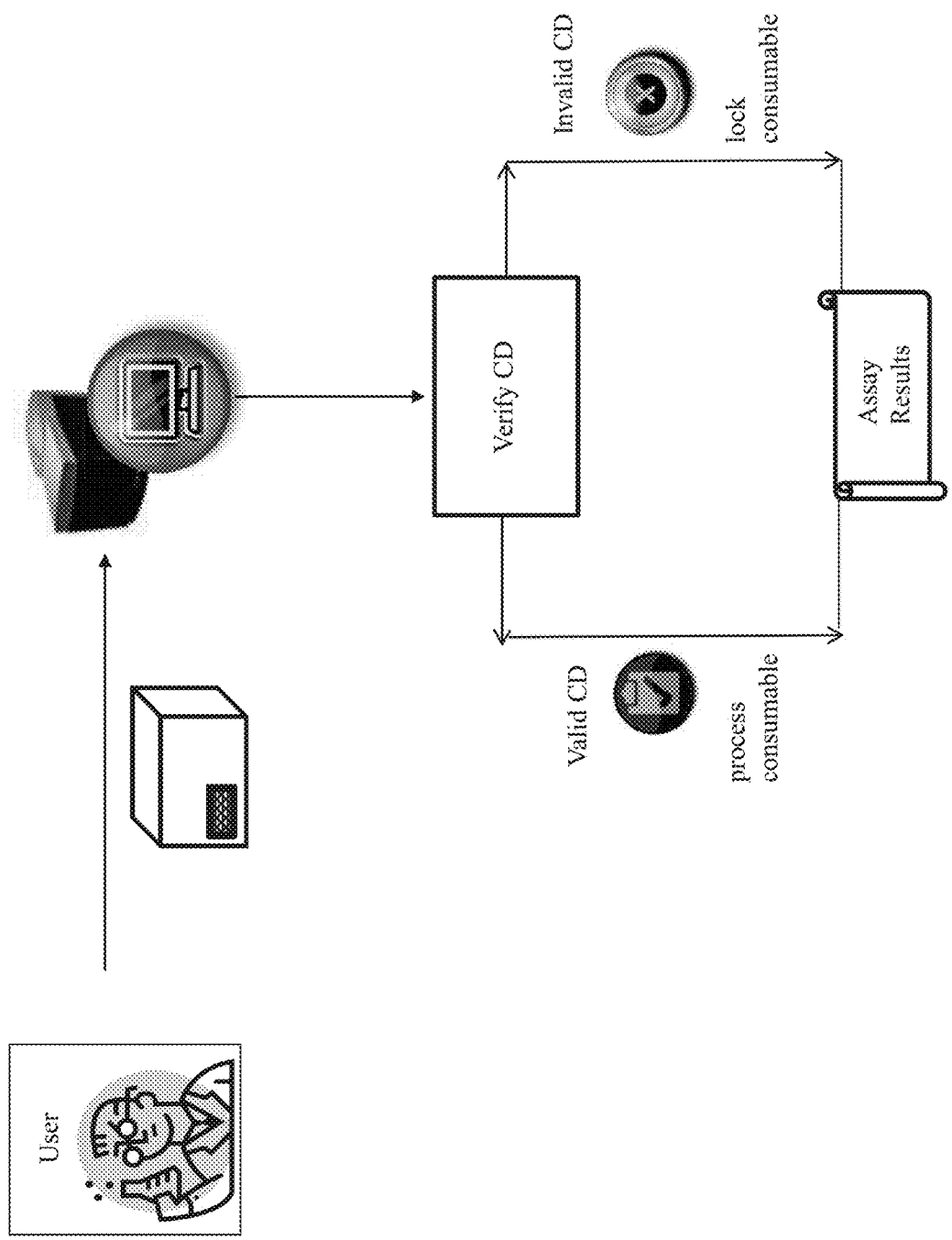
FIG. 3 the use of consumable data to verify authorized use of a consumable in an assay system.

FIG. 3 illustrates the verification of the consumable data by the system software and the consequences of that procedure. First, the customer inserts the consumable (301), with consumable identifier (302), into the system (303) (or otherwise contacts the consumable identifier with the controller on the system) and the system software identifies the consumable via the consumable identifier (302). The system will attempt to associate that identifier with the consumable data stored locally on the system repository. If the consumable data is verified and valid, the system will process the consumable and display the results of that processing step to the customer. But if the consumable data is invalid or unverifiable, although the consumable will be processed by the system, the results of that analysis will not be displayed or otherwise available to the customer until the consumable data is verified by the system software.

In addition, the invention provides a method of controlling customer access to an assay system and/or assay consumable by a vendor wherein the system comprises a system identifier, and the method includes receiving the system identifier from a customer, wherein the system identifier is sent to a vendor computing system; identifying the system identifier by the vendor; and performing an operation comprising:

(i) enabling full access to the apparatus and/or an assay consumable used in that apparatus;
(ii) enabling partial access to the apparatus and/or an assay consumable used in that apparatus; and
(iii) denying access to the apparatus and/or an assay consumable used in that apparatus.

The system identifier includes information that uniquely identifies the assay system, e.g., a serial number or other identification code that is generated and used by the vendor to identify the assay system. The system identifier is generated by the vendor during or after the manufacturing process and/or as the system is being prepared for shipment or transfer to a customer.

In one embodiment, the step of enabling access, either full or partial, includes the step of sending an access code from the vendor to the customer, thereby enabling access to the system. The access code can be a full or a partial access code that enables different functionalities in the system. In one embodiment, the access code is a partial access code that enables the system to operate in a demonstration mode. The partial access code can be time-limited. Alternatively, the access code can be a full access code that enables the system to be fully operational.

Figure 4:
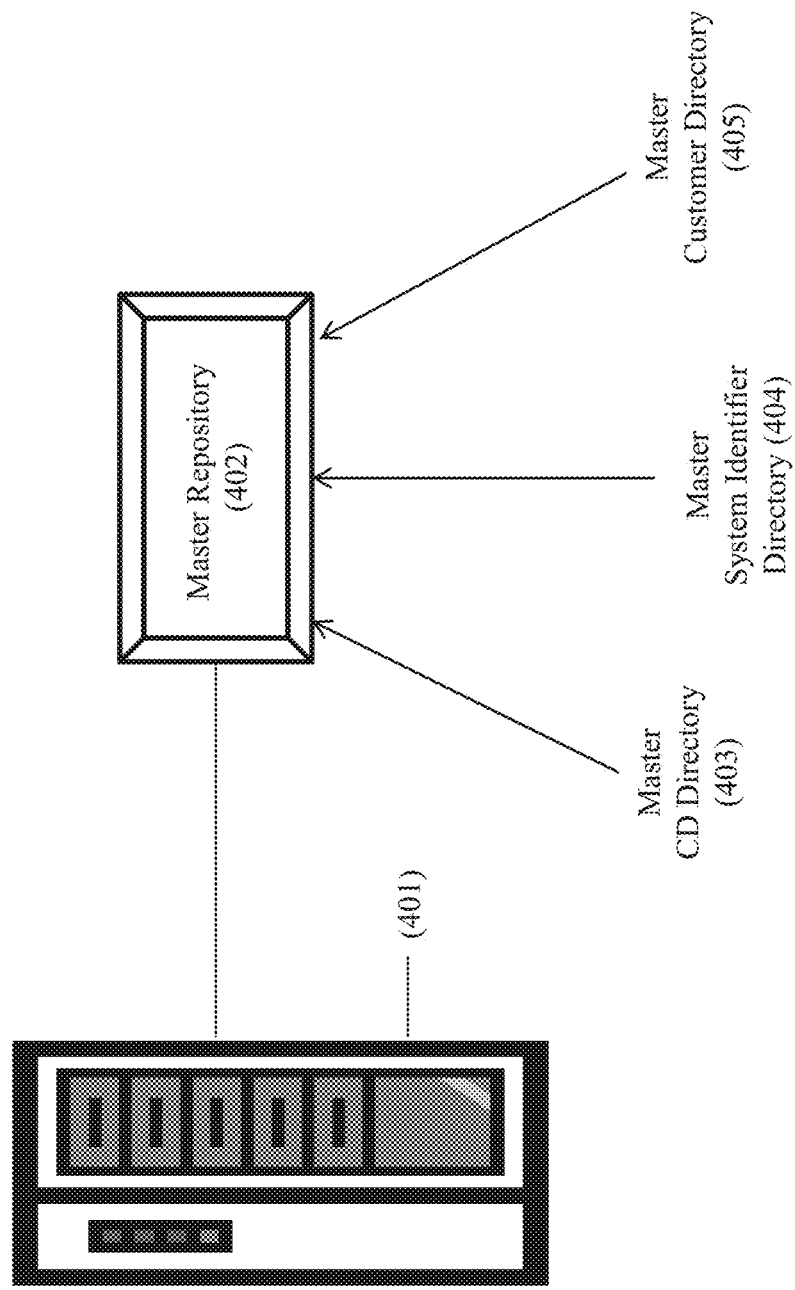
FIG. 4 illustrates the master repository on the CD server, its contents and/or interface with additional vendor directories.

As shown in FIG. 4, the CD server (401) includes a master repository (402) that comprises one or more directories of (i)

consumable data; (ii) system data; and (iii) customer data. In addition or alternatively, the data contained in or more of directories (i)-(iii) can be supplied to the master repository by an interface between the CD server and one or more supplemental vendor directories. In one embodiment, the master repository comprises (i) a master customer data directory (403); (ii) a master system identifier directory (404); and (iii) a master customer data directory (405). In a preferred embodiment, customer data is supplied to the CD server via an interface to a supplemental vendor-customer directory that maintains customer data. Customer data can be stored in one or more supplemental vendor-customer directories, each connected via an interface to the CD server. The master CD database comprises a plurality of CD directories, each generated for a consumable or lot of consumables. The master system identifier directory includes the unique system identifiers for each system manufactured and/or distributed by the vendor. And the master customer directory and/or supplemental vendor-customer directories that interface with the CD server include information related to each customer of the vendor, e.g., contact information for the customer and individual customers at that customer, billing information, pricing information, shipping information, order history, etc.

In a specific embodiment, when a system is manufactured and/or prepared for shipment, a vendor generates a system identifier for that system. The system identifier is stored in the master system identifier directory or available via an interface between a supplemental vendor directory to the CD server. If the system is ordered by a customer, order information, e.g., purchase order, a related quote, pricing, terms and conditions of sale or lease, related service agreements, etc., and customer information is stored to the master customer directory and/or to one or more supplemental vendor-customer directories that interface with the CD server. In this regard, the unique system identifier for that system is associated with the customer that has purchased that system in the master repository, as well as any information regarding related purchases by that customer. Shipping information for that system to the customer is also available in the customer directories(s) and once the system is shipped the customer receives a shipping confirmation, a copy of which is also stored in the customer directories. The customer receives the system and in a preferred embodiment, once installation and training on the system is completed, if required, the system software connects to the CD server via a remote interface between the system and the CD server to enable interaction between the two. The system initially connects to the CD server to confirm that system installation, and training is completed and successful and the CD server records that confirmation. Alternatively, if a remote connection is not enabled on the system, the customer receives a confirmation code, system login, and/or email address from the system once the system is installed and training is completed and the customer can login to the CD server via that confirmation code, system login and/or email, thereby providing a customer login to the CD server that provides a separate vendor-customer interface without a direct connection between the system and the CD server. The separate vendor-customer interface can be a portal on a vendor hosted customer accessible website via a password and/or the customer and the CD server can communicate via an email exchange server configured to send and receive emails between customers and the CD server (referred to collectively as an "indirect interface" between the customer and the CD server). Therefore, the vendor can communicate with the customer via a direct system-CD interface (referred to as a "direct interface") and/or via an indirect interface. As described above, the customer can then purchase consumables, the system will read the consumable identifier and confirm consumable data is stored locally, receive consumable data from the CD server, directly or indirectly, if necessary, and then the system will be enabled to use that consumable or lot.

Once the customer and vendor have a means of communicating via a direct or indirect interface, the customer and vendor can interact in a variety of ways and because the vendor has the ability to track customer-specific use information for the system and consumables purchase and/or used by the customer, communication between the parties can be more meaningful and productive. For example, the customer can browse and/or purchase vendor products, receive customer assistance, schedule service calls, etc. via the direct or indirect interface. Because the vendor is able to track customer activity and purchases so closely via the consumable identifier/CD server, the vendor can tailor its interactions with the customer based on that information. For example, because the vendor is aware of the customer's order history, the vendor can send the customer promotional materials for products related to those products the customer has purchased/used in the past. Similarly, because the vendor tracks information related to the customer's system, the vendor can send the customer preventative maintenance tips and reminders, general or specific customer training and seminars based on the customer's unique needs (and informed by tracking consumable data for that customer), and information regarding system service, warranty repairs, service contract information and reminders, etc.

In one embodiment, the vendor tracks use of consumables by an assay customer and the consumable data stored to the assay system includes system-consumable use information. To facilitate consumable use tracking, the assay system is configured to send system-consumable use information directly or indirectly to the CD server. If a direct interface is enabled between the system and the CD server, system-consumable use information can be sent automatically. If, however, the direct interface is not enabled, system-consumable use information can be provided indirectly by the customer to the CD server. In this embodiment, the system can periodically prompt the customer to provide system-consumable use information to the vendor via the indirect interface. The vendor can maintain a directory of customer consumable information to track consumable use and information from that directory is used to send consumable data, via the direct or indirect interface, that can be relevant to a customer based on prior consumable and/or system use. If the direct interface is enabled, the assay system can be configured to receive assay system maintenance and/or promotional information from a vendor computing system related to an individual customer's prior consumable and/or system use.

The vendor can also track and/or convey system maintenance information to the customer, e.g., monitoring system and/or system components usage, service history, system troubleshooting information, the results of diagnostics run on the system, control charting, periodic maintenance scheduling, warranty information regarding the system and/or a components thereof, or combinations thereof. The system software can be programmed to monitor various components of the system and automatically or when prompted, send monitoring reports to a remote computing system and/or to a service technician. If a direct interface is not enabled, the system can prompt the customer to send monitoring reports to the CD server via an indirect interface. In addition or alternatively, such system monitoring reports can be accessed by a service technician charged with the task of maintaining and/or servicing the system on site or remotely. In a specific embodiment in which a direct interface is enabled, the CD server monitors system component usage and/or warranty information and based on standard system component lifetimes and/or warranty terms, schedules periodic system/component maintenance and/or upgrades by a service technician. In addition, the CD server can maintain a log of the service history for a given assay system and schedule a service call by a service technician (this can be done using either a direct or indirect interface). The remote computing system can also send an individual assay system software upgrades via a direct or indirect interface.

In addition, one or more of the following system components and/or actions can be monitored by the system software including, but not limited to, expected motor positions during normal usage, positional errors for each expected motor position, corrective actions and/or attempted corrective actions taken by the system in the event of a motor positioning error, and error frequencies; component usage, e.g., the approximate time the component has been on in the system, and in a preferred embodiment, the system also tracks the relative lifespan of that component under normal use conditions; locking mechanisms attempts, re-attempts, and failures; bar code reader attempts, re-attempts, and failures; approximate temperature of one or more components in the system, error warnings, database performance and capacity, instrument hard disk capacity, software and firmware version and patches, customer login/logout, system startup and shutdown, and the like. In a particularly preferred embodiment involving a system designed to conduct electrochemiluminescence measurements using assay consumables, the system software can also be programmed to monitor the time the camera has been on and approximate temperature, the use cycle of latches within the system, bar code reader attempts, re-attempts, and failures, consumable locking and unlocking events, ECL waveform voltage and integrated current, image processing analysis accuracies and failures, consumable type, kit, owner, bar code, and time stamp for each consumable run in the system, or combinations thereof. Still further, the system software can also monitor experiments conducted in the system, e.g., when, by whom, and which type of consumable(s) were used in that experiment. Such system-use monitoring information can be sent via a direct and/or indirect interface, to the CD server to enable the vendor to schedule appropriate support, service and/or maintenance on the system.

In another embodiment, by tracking use of an assay system, a vendor can provide use and/or purchasing assistance. For example, a vendor can track consumable use and purchase history and based on the consumable data for a given lot or consumable, the vendor can monitor the expiration data of a given lot or consumable and notify the customer of an approaching expiration date for a lot or consumable. Tracking use of an assay system/consumable type can also enable a vendor to track a relative schedule/frequency of consumable use and notify the customer that the customer's consumable supply needs to be replenished. If a direct interface is enabled, the system can also be configured to order/re-order consumables and the system can be further configured to track and confirm consumable orders from a vendor. If a direct interface is not enabled, the system can monitor consumable use and inventory and prompt the customer to replenish a supply of one or more consumables. (In this regard, a system receives lot size information via the consumable identifier and by monitoring consumable usage, it can prompt the customer when the available consumable supply in a given lot has been diminished to a minimum level.) Moreover, by tracking consumable use, the vendor can send the customer information regarding custom assay design services for a specific custom consumable type based on the customer's order/consumable use history. A direct or indirect interface can also provide customer training modules, consulting services, and/or live customer service assistance capabilities to facilitate the customer experience (i.e., live-chatting) (referred to collectively as system and/or consumable technical support information).

In another embodiment, tracking consumable/system use enables the vendor to send promotional material to the customer, e.g., when a new type or lot of consumables historically used by a given end-customer, the vendor computing system sends consumable data to the customer regarding those new products. Such promotional materials can also relate to new assay systems that might be of interest to the customer based on that customer's prior usage. The remote computing system can also send a customer literature references that can relate to one or more consumables/systems used by a given customer.

These and other specific examples of consumable data are described in more detail hereinbelow.

Assay Systems, Consumables & Methods of Use

The assay systems contemplated by the present invention are used to conduct any type of diagnostic or analytical method known in the art. Such analytical methods include but are not limited to clinical chemistry assays (e.g., measurements of pH, ions, gases and metabolites), hematological measurements, nucleic acid amplification assays (e.g., polymerase chain reaction (PCR) and ligase chain reaction assays), immunoassays (e.g., direct, sandwich and/or competitive immunoassays and serological assays), oligonucleotide ligation assays, and nucleic acid hybridization assays. Any biological reagent that might be used in such analytical methods can be used in such systems, including but not limited to nucleic acids, nucleotides, oligonucleotides, DNA, RNA, PNA, primers, probes, antibodies or fragments thereof, antigens, small molecules, e.g., drugs or prodrugs, streptavidin, avidin, and biotin.

These systems can be portable, e.g., hand-held, and/or operated within a fixed laboratory or field setting, alone or in combination with one or more additional components, assay devices or systems. These systems can be used in a variety of applications, from field operations to laboratory settings, in a wide variety of industries, including but not limited to, medical, clinical, forensic, pharmaceutical, environmental, veterinary, biological, chemical, agricultural, waste management, hazardous chemical, drug testing, and in defense applications, e.g., for the detection of biological warfare agents. The assay systems and consumables used in the present invention can detect an analyte of interest by any suitable method, including but not limited to, optical, electromechanical, radiowave, electromagnetic, colorimetric, fluorimetric, chemiluminescent, electrochemiluminescent, radiochemical, nuclear magnetic resonance, enzymatic, fluorescent, particle-count, and cell-count based detection.

The assay consumable includes devices in which one or more steps of an assay process are conducted and such devices can include one or more test sites where an assay measurement is conducted. In one embodiment, the assay consumable includes at least one assay test site for an assay. A test site can include a plurality of distinct assay domains, at least two of the domains including reagents for measuring different analytes. Still further, the consumable can include a plurality of test sites for a plurality of individual assays. Alternatively, the assay consumable can be a component that provides a reagent or other assay component that is used by the system to conduct an assay. For example, the assay consumable can be a container with one or more compartments for holding assay reagents. The assay consumable (or test sites therein) can be single use or it can be reusable. The assay consumable can be configured to conduct one test or multiple tests (sequentially or in parallel).

Test sites, as used herein, refer to regions of a consumable that hold, contact and/or interrogate a sample. A test site can include a plurality of distinct assay domains, at least two such domains include reagents for measuring different analytes. Consumables can comprise multiple test sites which can hold, contact or otherwise interrogate distinct volumes (aliquots) of the same sample and/or volumes of different samples. A sector of an assay consumable refers to grouping of two or more test sites of the consumable. Each test site can be used to conduct a single measurement or multiple measurements on a volume of sample (for example, the measurement of multiple different analytes in a multiplexed assay format). Depending on the specific requirements of an application, a consumable with multiple test sites can be configured to use all of its test sites in parallel, to use its test sites at different times (e.g., assigning unused test sites to be used as new samples are delivered to the assay system), or a combination of both modes of operation can be enabled.

The assay consumable can be any structure useful in diagnostic applications and that structure can be dictated by the particular assay format or detection method employed by the device. Examples of assay consumables suitable for use with the invention include, but are not limited to, test tubes, cuvettes, flow cells, assay cartridges and cassettes (which can include integrated fluidics for assay processing), multi-well plates, slides, assay chips, lateral flow devices (e.g., strip tests), flow-through devices (e.g., dot blots), pipette tips, solid phase supports for biological reagents and the like. In certain embodiments, test sites in the assay consumable are defined by compartments in the assay consumable, e.g., wells, chambers, channels, flow cells and the like. The assay consumable and/or test sites can include one or more components used to carry out an assay measurement according to one or more specific detection methodologies. Depending on the function of the consumable and the detection modalities employed by the assays system, examples of such components can include, but are not limited to, lateral flow matrices, filtration matrices, optical windows, sensors (e.g., electrochemical and optical sensors), solid phase supports for binding reactions (e.g., coated slides, chips, beads, pins, coated filtration or lateral flow matrices, tubes and the like), reagents (dry or in liquid form), electrodes, analyte selective membranes and the like.

In one embodiment, the assay consumable can be a device that incorporates a conventional lateral flow test strip, e.g., an immunoassay test strip, as an assay medium. In this example, the device is molded to include an identifier or the identifier is affixed to the device without any modification to the structure of the device and/or the assay medium. In one embodiment, the device is placed within the analytical system, i.e., the assay system, for analysis and before, during or after the performance of the assay, the identifier controller within, affixed to or associated with the assay system reads the data contained on the identifier and uses that data in the assay or after the assay is completed by the system.

In another embodiment, the assay consumable and accompanying assay system or reader is capable of performing a multiplex assay. A multiplex assay is a type of assay in which multiple measurements are performed on a single sample, e.g., by distributing samples across multiple test sites and/or by carrying out multiple measurements on volumes of samples in individual test sites. The multiple measurements can include, but are not limited to, (i) multiple replicates of a measurement for an analyte; (ii) multiple measurements of a certain analyte (i.e., multiple non-identical measurements for the same analyte, e.g., measurements that differ in format or in the identity of the assay reagents that are employed); and/or (iii) measurements of multiple different analytes. In one specific embodiment, an assay consumable is configured to carry out, in one or more test sites, multiplex measurements that include at least two assays for two different analytes.

The invention is not restricted to specific approaches for conducting multiplex measurements in a test site and can employ any of the numerous techniques that have been developed for carrying out multiplex measurements. Multiplex measurements that can be used with the invention include, but are not limited to, multiplex measurements (i) that involve the use of multiple sensors; (ii) that use discrete assay domains on a surface (e.g., an array) that are distinguishable based on location on the surface; (iii) that involve the use of reagents coated on particles that are distinguishable based on a particle property, such as size, shape, color, etc.; (iv) that produce assay signals that are distinguishable based on optical properties absorbance or emission spectrum), (v) that are based on temporal properties of an assay signal (e.g., time, frequency or phase of a signal), and/or (vi) that are based on some other assay characteristic. Accordingly, interpretation of multiplexed assay results can involve the use of multiplexing information, such as the identity of the assays carried out in each test site and, within a test site, any assay characteristics (identity of specific sensors, location and identity of assay domains, etc.) that are used to distinguish assays carried out in a test site and/or that are used to tie a specific assay identity to the corresponding assay signal.

In one embodiment, an assay test site comprises a plurality of distinct assay domains and each domain comprises one or more reagents for measuring a different analyte. Multiplexing information, including the location, identity, and composition of each assay domain, is used to identify the assay signal generated at each domain and connect it to a determination of the presence or amount of the corresponding analyte (a process which can include the application of additional consumable data such as signal thresholds and/or calibration parameters). Such multiplexing information can be provided as consumable data and/or stored to the consumable identifier.

A test site can be configured to carry out a plurality of multiplexed measurements (e.g., it can include a plurality of distinct assay domains, wherein each domain comprises reagents for measuring a different analyte). In one embodiment, the assay consumable can include a plurality of test sites. Information regarding the exact configuration of the one or more test sites, assay domains, and/or one or more sectors in a consumable can be included in the information saved to the assay consumable identifier and/or provided as consumable data. This information can include the location and identity of the test sites, assay domains, and/or one or more sectors as well as multiplexing information (as described above) including the number, identity and differentiating characteristics of the individual measurements within a test site, assay domain, and/or sector (e.g., the specific locations, identities and/or assay reagents of assay domains within each test site). In addition, the use of a test site, assay domain, and/or sector in an assay consumable can also be recorded to the identifier to track the use of the consumable in an assay system. The identifier and/or consumable data can also include information concerning the assay format and specific processing steps to be used for an assay consumable or test site, assay domain, and/or sector of an assay consumable. The identifier and/or consumable data can also include information concerning analytical methods that should be applied by the system once an assay is conducted to analyze the output of an assay in a given test site, assay domain, and/or sector and, optionally, to provide results that combine the output from multiple assays in a test site, assay domain, and/or sectors.

The test sites can be configured in any suitable configuration, depending on the geometry of the consumable and/or the type of assay conducted with the consumable. In one embodiment, the test sites are configured as wells and/or chambers in the assay consumable. For example, the assay consumable of the present invention can be a multi-well plate (e.g., a 24-, 96-, 384- or 1536-well plate), and the wells of the plate can further comprise a plurality (e.g., 2 or more, 4 or more, 7 or more, 25 or more, 64 or more, 100 or more, etc.) of distinct assay domains. Multi-domain multi-well plates that are adapted to allow assay measurements to be conducted using electrode induced luminescence measurements (e.g., electrochemiluminescence measurements) are described in U.S. application Ser. No. 10/238,391, entitled "Methods and Reader for Conducting Multiple Measurements on a Sample", filed on Sep. 10, 2002, hereby incorporated by reference. The exact configuration of the domains, test sites, and/or sectors in an assay consumable, as well as the specific identity of each domain, test site, and/or sector and the reagents bound to that domain/test site/sector can be included in the information saved to the assay consumable identifier and/or provided as consumable data. In addition, the use of a given domain, test site, and/or sector in an assay consumable can also be recorded to the identifier to track the use of the consumable in an assay system.

Assay consumables can be used in a plurality of diverse assays and this diversity leads to a variety of suitable configurations of the associated consumable. In one assay format, the same analyte is measured at different assay domains within a test site, the different assay domains being designed to measure a different property or activity of the analyte. Information concerning the assay format that can be used in an assay consumable, test site and/or assay domain can also be saved to the assay consumable identifier and/or provided as consumable data. The identifier and/or consumable data can also include information concerning analytical methods that should be applied by the system once an assay is conducted to analyze the output of an assay in a given test site and/or domain and compare that output to an assay in a separate test site and/or domain.

One example of a multiplex assay consumable and reader is described in U.S. 2004/0022677, the disclosure of which is incorporated herein by reference in its entirety. Such assay consumables include one or more, and in one embodiment, a plurality of test sites and/or assay domains for conducting one or more assay measurements simultaneously or sequentially. For example, the test sites can be configured as wells and/or chambers. These test sites and/or assay domains comprise one or more electrodes for inducing luminescence from materials in the test sites and/or assay domains. The assay consumables can further comprise assay reagents in liquid or dry form, e.g., in the test sites, e.g., wells or chambers, of the consumable.

In addition to the test sites and assay domains, an assay consumable or multi-well assay plate can include several additional elements, e.g., a plate top, plate bottom, wells, working electrodes, counter electrodes, reference electrodes, dielectric materials, electrical connections, and assay reagents. The wells of the plate can be defined by holes or openings in the plate top, or as indentations or dimples on a surface of a plate. The plates can have any number of wells of any size or shape, arranged in any pattern or configuration and can be composed of a variety of different materials. Exemplary embodiments of consumables that can be used in the present invention include industry standard formats for the number, size, shape and configuration of the plate and wells, e.g., 96-, 384-, and 1536-well plates, with the wells configured in two-dimensional arrays. Other formats can include single well plates, 2-well plates, 6-well plates, 24-well plates, and 6144-well plates. Multi-well assay plates can be used once or can be used multiple times and are well suited to applications where the plates are disposable. Various configurations for suitable assay plates can be used in the present invention, including but not limited to those depicted in FIGS. 11A, 12A, 13A, 13B, 14A, 15, and 16A of U.S. Application Ser. No. 2004/0022677, each of which are incorporated herein by reference. As stated above, the specific configuration and identity of assay test sites, domains, and/or sectors of an assay consumable can be included in the information saved to the assay consumable identifier and/or provided as consumable data.

In this embodiment, the assay consumables can be used in a reader that can be used to induce and measure luminescence, e.g., electrode induced luminescence or electrochemiluminescence, in assays conducted in or on assay consumables, e.g., multi-well assay plates. The accompanying assay system can also induce and/or measure current and/or voltage, for example, at an electrode. The assay system can incorporate, for example, one or more photodetectors; a light tight enclosure; mechanisms to transport the assay plates into and out of the reader (and in particular, into and out of a light tight enclosure); mechanisms to align and orient the assay plates with the photodetector(s) and/or with electrical contacts; additional mechanisms to track and identify plates (e.g. bar code readers); mechanisms to make electrical connections to plates, one or more sources of electrical energy for inducing luminescence, and appropriate devices, electronics and/or software. The assay reader can also include mechanisms to store, stack, move and/or distribute one or more multi-well assay plates (e.g. plate stackers and/or plate conveyors). The assay system can be configured to measure light from multi-well assay plates by measuring light sequentially from a plurality of sectors or regions of the plate (i.e., a grouping of a plurality of adjacent assay domains within a plate) and/or from the entire plate substantially simultaneously or simultaneously. The assay system can also incorporate additional microprocessors and computers to control certain functions within the system and to aid in the storage, analysis and presentation of data. Various configurations for suitable assay systems can be used in the present invention, including but not limited to those depicted in FIGS. 17 to 23 of U.S. Application Ser. No. 2004/0022677, each of which are incorporated herein by reference.

The additional microprocessors and computers in the assay system can also interact with the assay consumable identifier microprocessor or controllers by transferring data and commands to/from the identifier to the various microprocessors/controllers throughout the system to perform various operations of the components listed above within the assay system.

The system can adjust the assay parameters prior to initiating an assay based on the consumable data saved to the identifier and/or stored or provided as consumable data via a direct or indirect interface. Thereafter, the system makes the appropriate electrical, fluidic and/or optical connections to the consumable (making use of electrical, fluidic and/or optical connectors on the consumable and system) and conducts an assay using the consumable. The sample can be introduced into the consumable prior to inserting the consumable in the system. Alternatively, the sample is introduced by a component of the system after the consumable is inserted in the system. The assay can also involve adding one or more assay reagents to the consumable and instructions for adding those various assay reagents can be saved to the identifier and/or provided as consumable data and the system adds those reagents to the consumable before or during the assay according to the instructions saved to the assay consumable identifier and/or provided as consumable data.

Alternatively, the assay consumable is a cartridge and the consumable further comprises an element selected from one or more fluidic components, one or more detection components, one or more assay cells, reagents for carrying out an assay, working electrodes, counter electrodes, reference electrodes, dielectric materials, electrical connections, dried and/or liquid assay reagents, or combinations thereof. The cartridge can further comprise at least one assay cell that comprises a plurality of distinct assay test sites and/or domains, each of these test sites and/or domains comprising reagents for measuring a different analyte.

An example of an assay consumable cartridge that can be used in the present invention is described in US Application Ser. No. 2004/0189311, the disclosure of which is incorporated herein by reference in its entirety. The assay consumable described therein is an assay cartridge that incorporates one or more fluidic components such as compartments, wells, chambers, fluidic conduits, fluid ports/vents, valves, and the like and/or one or more detection components such as electrodes, electrode contacts, sensors (e.g. electrochemical sensors, fluid sensors, mass sensors, optical sensors, capacitive sensors, impedance sensors, optical waveguides, etc.), detection windows (e.g. windows configured to allow optical measurements on samples in the cartridge such as measurements of absorbance, light scattering, light refraction, light reflection, fluorescence, phosphorescence, chemiluminescence, electrochemiluminescence, etc.), and the like. Such consumables can also comprise reagents for carrying out an assay such as binding reagents, detectable labels, sample processing reagents, wash solutions, buffers, etc. The reagents can be present in liquid form, solid form and/or immobilized on the surface of solid phase supports present in the cartridge. In this embodiment, the consumables include all the components necessary for carrying out an assay. In addition, the assay consumable is used in connection with a consumable reader adapted to receive the consumable and carry out certain operations on the consumable such as controlling fluid movement, supplying power, conducting physical measurements on the cartridge, and the like.

More specifically, such assay consumable cartridges have one or more assay test sites (e.g., wells, compartments, chambers, conduits, flow cells, etc.) that can include one or more assay domains (e.g., discrete locations on a assay test site surface where an assay reaction occurs and/or where an assay dependent signal, such as an electrochemical or an electrode induced luminescence signal is induced) for carrying out a plurality of assay measurements. In this embodiment, assay domains are supported on assay electrodes (in one embodiment, an array of assay electrodes, e.g., a one dimensional array of assay electrodes) so as to permit the conduct of assays based on electrochemical or electrode induced luminescence measurements. The assay domains are, optionally, defined by a dielectric layer deposited on the electrodes. In addition, the assay consumables can have one or more attributes that make them suitable for use in "point of care" clinical measurements, e.g., small size, low cost, disposability, multiplexed detection, ease of use, etc.

The assay consumable cartridge can comprise the necessary electronic components and/or active mechanical components for carrying out an assay measurement, e.g., one or more sources of electrical energy, ammeters, potentiometers, light detectors, temperature monitors or controllers, pumps, valves, etc. Alternatively, some or all of the electronic and/or active mechanical components are arranged within a separate assay reader. The reader would also have the appropriate electrical, fluidic and/or optical connections to the assay consumable for carrying out an assay using the consumable. Using such an arrangement, the assay consumable can be designed to be low cost and disposable while the reader (which holds the more expensive and complex components) reusable.

In one embodiment, a cartridge-based biochemical detection system can include a system housing comprising an optical detector wherein the system housing is adapted and configured to receive and position the assay consumable and/or the optical detector for processing. The system can further comprise support subsystems that can include one or more of the following: storage subsystem for storing assay reagents/consumables and/or waste; sample acquisition/preprocessing/storage subsystem for sample handling; fluidic handling subsystem for handling the reagents, sample, waste, etc. and for providing fluids to the detection chamber via a fluid inlet line; electrical subsystem for electrically contacting the cartridge's electrical contacts and supplying electrical energy to the electrodes; and a control subsystem for controlling and coordinating operation of the system and subsystems and for acquiring, processing and storing the optical detection signal. The information stored to the assay consumable identifier and/or provided as consumable data can include information that is used to control or adjust one or more of the assay system components prior to and/or during the conduct of an assay using the assay consumable.

Still further, the assay consumable can be a container holding one or more assay reagents, including but not limited to one or more buffers, diluents, and/or reagents used by the assay system in the conduct of an assay. The assay consumable identifier can be affixed to the container and/or affixed to a packaging for the container.

Assay Consumable Identifier

In one embodiment, the assay consumable identifier comprises memory for storing information related to the consumable, its history and/or its use. In one embodiment, the memory is non-volatile memory. Non-volatile memory is computer memory that can retain the stored information without power. Examples of non-volatile memory which can be used in the consumable identifier include, but are not limited to, electronic non-volatile memory (e.g., read-only memory and flash memory), magnetic memory (e.g., hard disks, floppy disk drives, and magnetic tape), optical memory (optical disc drives) and hybrids of these approaches (e.g., magneto-optical memory).

In one embodiment, the assay consumable identifier comprises EPROM (erasable programmable read-only memory), a type of programmable read-only memory that can be erased by exposing it to ultraviolet light. Once erased, it can be reprogrammed with new or modified data. In another embodiment, the assay consumable identifier comprises EEPROM (electronically erasable programmable read-only memory) a class of non-volatile electronic memory that can be electrically erased and reprogrammed without exposure to UV light. An EEPROM can be written to or programmed more than once and can be selectively programmed (the customer can alter the value of certain cells without erasing the programming of the other cells). Therefore, sections of data can be erased and replaced without needing to alter or reinstall the rest of the chip's programming.

In another embodiment, the assay consumable identifier comprises flash memory, a specific type of EEPROM that is erased and programmed in large blocks. Although flash memory is technically a type of EEPROM, the term "EEPROM" is generally used to refer specifically to non-flash EEPROM which is erasable in small blocks, typically bytes. Because erase cycles are slow, the large block sizes used in flash memory erasing give it a significant speed advantage over conventional EEPROM when writing large amounts of data.

In another embodiment, the assay consumable identifier comprises a smart card, chip card, or integrated circuit card (ICC) (referred to collectively as "ICCs"). These are small cards with embedded integrated circuits which can process and store data. There are two broad categories of ICCs; i) "memory cards" that contain non-volatile memory storage components and, optionally, some specific security logic but do not contain microprocessors and Ii) "microprocessor cards" that combine non-volatile memory components with microprocessor components and enable the processing of information being read into or out of the ICC. The ICC electronic components are supported on a card that is, typically, made of plastic such as PVC or ABS. The card can include an embedded hologram to avoid counterfeiting. Contact ICCs have conductive contact pads. When inserted into a reader, the contact pads on the ICC make contact with electrical connectors in the reader to allow for transfer of information between the reader and the ICC, for example, allowing the reader to read, erase or write information on the ICC.

Another method of transferring information is via an RFID, i.e., radio frequency identification, which is similar in theory to bar code identification. With RFID, the electromagnetic or electrostatic coupling in the RF portion of the electromagnetic spectrum is used to transmit signals. An RFID system consists of an antenna and a transceiver, which read the radio frequency and transfers the information to a processing device, and a transponder, or tag, which is an integrated circuit containing the RF circuitry and information to be transmitted.

Identification can also be accomplished by reading a bar code. One of the key differences between RFID and bar code technology is that RFID eliminates the need for line-of-sight reading that bar coding depends on. Also, RFID scanning can be done at greater distances than bar code scanning. High frequency RFID systems (850 MHz to 950 MHz and 2.4 GHz to 2.5 GHz) offer transmission ranges of more than 90 feet, although wavelengths in the 2.4 GHz range are absorbed by water (the human body) and therefore has limitations.

In one embodiment, the non-volatile memory used in the present invention is comprising an EEPROM, flash memory, ICC or combinations thereof. In one embodiment, the non-volatile memory is an EEPROM. In an alternate embodiment, the non-volatile memory is an RFD.

In an additional alternative embodiment, two or more non-volatile memory components can be used in the present invention. For example, a first assay consumable comprising a first identifier can be used in the assay system, and an additional assay consumable comprising an additional identifier can also be used in the assay system. Each identifier can include the same or different type of memory. However, for each different form of memory, there will be a separate identifier controller. And certain consumable data can be stored on one identifier and other consumable data on an additional identifier of the same or different type. For example, one assay consumable used in the system can comprise an EEPROM or RFID as an identifier, whereas the system can also use an additional assay consumable comprising, e.g., a bar code as a identifier. The assay system would comprise an identifier controller capable of interfacing with the first identifier, i.e., the EEPROM or RFID, and the system will further comprise an additional controller that will interface with the bar code.

The assay system of the present invention includes an identifier controller that controls the operation of the non-volatile memory and other components of the assay system. The identifier controller optionally includes a micro-controller to interface with the non-volatile memory over a communication interface, which can incorporate conventional interface architectures and protocols such as I²C, a two line serial bus protocol. The microcontroller addresses the non-volatile memory and performs write, read and erase operations on the memory.

The consumable identifier can be located on the consumable or it can be a separate component. In either case, the system can be designed to have a unique identifier for each consumable. Alternatively, the system can be configured so that one separate consumable identifier is used to hold information relating to a plurality of consumables. In one example, each package of consumables has a package-specific identifier mounted on the package (or, alternatively, supplied in the package) that holds information relating to the plurality of consumables in the package. Optionally, each consumable also carries an additional unique consumable-specific identifier attached to the consumable. This consumable-specific identifier is used primarily to uniquely identify the consumable and link it to information on the package-specific identifier. In this embodiment, lot information content and/or non-editable identifiers such as bar codes can be used.

The various components of the assay system can be housed together in a single unit or can be housed separately. For example, the assay system can include an assay reader and an identifier controller as separate units. The assay system provides for communication (which can be wired or wireless communication) directly between the assay reader and identifier controller or, alternately, indirectly through additional components of the assay system. In an alternative embodiment, the identifier controller is housed within the assay reader. In such an embodiment, the assay reader can be configured such that insertion of the consumable into the reader during the conduct of an assay also enables communication between the consumable identifier and the identifier controller (e.g., a port into which the consumable is inserted includes components for processing and/or reading the consumable and also includes components, such as electrical contacts or a radio transmitter, for communicating with the consumable identifier). In one example, when the consumable is loaded into the assay system, electrical contacts are made between the controller and the identifier, e.g., non-volatile memory. The controller is then able to read, erase and/or write consumable data to the identifier. Alternatively, the assay reader can have separate ports for processing/reading a cartridge and for communicating with the consumable identifier. The customer places the assay consumable or packaging in or in proximity to the controller port such that the controller makes electrical contact with the identifier to enable the controller to read, erase and/or write consumable data to the non-volatile memory.

In one embodiment, the identifier comprises non-volatile memory comprising an RFD tag, a bar code, an EPROM, and EEPROM. Still further, the identifier can comprise an EEPROM comprising flash memory and ICC.

The methodologies of the present disclosure may be provided and/or implemented on one or more processors, and for example, also may be provided via web-based and/or cloud computing framework.

A computer readable medium may include any tangible device that can store a computer code or instruction that can be read and executed by a computer or a machine. Examples of computer readable medium may include, but not limited to, hard disk, diskette, memory devices such as random access memory (RAM), read-only memory (ROM), optical storage device, and other recording or storage media.

Consumable Data

The identifier is programmed, e.g., during the manufacturing process or when the consumable is prepared for shipment. The identifier can be programmed with consumable data which can be used before, during or after an assay or a step of a multi-step assay to control the operation of the assay system, reader or a component of the assay system. In addition or alternatively, some or all of the information required for use of a given consumable can be provided as consumable data. The term "consumable data" can include any information used to uniquely identify a particular assay or assay step, assay consumable, consumable domain(s), biological reagent or sample or to distinguish a particular assay, assay step, assay consumable, consumable domain(s), biological reagent or sample from other assay consumables, consumable domains, biological reagents or samples. Consumable data can include consumable information, sample information, chain of custody information, consumable/test site information, assay process information, consumable security information, or combinations thereof. Consumable data can further include information related to one or more analytical tools that can be applied by the system to analyze data generated during and/or after the conduct of an assay, assay system maintenance information, system-consumable promotional information, and/or system and/or consumable technical support information.

Each type of consumable data is described in more detail below and it should be understood that each type of consumable data can be stored to the consumable identifier and/or provided as consumable data.

Consumable Identification & Configuration Information

Consumable data can include consumable identification and configuration information that includes but is not limited to lot identification information, lot specific analysis parameters, manufacturing process information, raw materials information, expiration date, Material Safety Data Sheet (MSDS) information, product insert information (i.e., any information that might be included or described in a product insert that would accompany the assay consumable, e.g., the assay type, how the assay is performed, directions for use of the assay consumable, assay reagents, or both, etc.), threshold and/or calibration data for one or more reagents used in the assay consumable or in an assay or a step of a multi-step assay, and the location of individual assay reagents and/or samples within one or more test sites of the assay consumable.

The consumable data can also include lot identification information, i.e., information that is used to identify a particular lot of assay consumables, which is distinct from lot-specific analysis parameters, which includes that information that is unique to a given lot that can be used by the system, e.g., to conduct an assay with a consumable from that lot or to analyze assay results derived from a consumable from that lot. In one embodiment, if the assay consumable is a multi-well assay plate or a cartridge, the lot-specific analysis parameters can include, but are not limited to, the following: (i) the revision level that determines the schema used to interpret the information; (ii) the consumable type; (iii) the date of manufacture; (iv) the lot number; (v) the date of expiration; (vi) a cross-talk correction matrix, to account for chemical cross-reactivity; (vii) a threshold for assays to be conducted in the consumable and each internal negative control; (viii) a range for each internal positive control; (ix) ranges for each assay to be conducted in the cartridge for the positive control sample; (x) a software checksum to ensure integrity of the data; (xi) in-well (or in-test site) control acceptance ranges; (xii) assay names and/or identifiers; (xiii) information concerning assay quality control, including negative and positive quality control materials that are used to verify the operation of the reader and the consumable; (xiv) calibration information such as a master calibration curve; and (xv) number and names of assay calibrators and/or assay calibrator acceptance ranges.

The consumable data can include sample information, such as the location of samples within at least one test site of the assay consumable, assay results obtained on the assay consumable for the sample, and the identify of samples that have been and/or will be assay in the assay consumable The consumable data can also relate to chain of custody, e.g., information regarding the control, transfer and/or analysis of the sample and/or an assay consumable. Chain of custody information can be selected from customer identification, sample identification, time and date stamp for an assay, the location of the assay system in a laboratory during the assay, calibration and QC (quality control) status of the assay system during the assay, custody and/or location information for the assay consumable before and after the conduct of the assay, assay results for a given sample, as well as customer created free text comments input before, during or after an assay is processed by the system. Still further, chain of custody information can include time, date, manufacturing personnel or processing parameters for one or more steps during the manufacture of the assay consumable, custody, location and/or storage conditions for the assay consumable following manufacture and/or between steps during the manufacture of the assay consumable.

Consumable data can also include consumable/test site information, such as consumable type and structure, the location and identity (e.g., the structure, composition, sequence, concentration and/or origin) of assay reagents included within an assay consumable, and the location and identity of assay reagents within an assay test site of the assay consumable. The consumable data can be used to distinguish a first test site within that consumable from a different test site within the consumable. Still further, the consumable data can include sample information comprising the location of samples within at least one test site of the assay consumable; assay results obtained on the assay consumable for the sample; identity of samples that have been and/or will be assayed in the assay consumable; or combinations thereof. Additionally, the consumable data is consumable/test site information comprising consumable type and structure; location and identity of assay reagents included with the assay consumable; location and identity of assay reagents within an assay test site of the assay consumable; or combinations thereof.

In an additional embodiment, consumable/test site information can include information concerning assays previously performed by a reader on one or more test sites of the consumable, and information concerning assays to be performed by a reader on one or more test sites within the consumable. Therefore, once the assay is conducted by the system, the controller can be used to write the results of the assay to the identifier. Such information includes, but is not limited to raw or analyzed data collected by the system during the assay (wherein analyzed data is data that has been subjected to statistical analysis after collection and raw data is data that has not been subjected to such statistical analysis), a list of test sites and/or domains within the assay consumable used during a given assay, a schedule of events to be conducted on an assay consumable or a test site and/or domain within an assay consumable, a list of those test sites and/or domains of the assay device that have not be subjected to an assay, assay or system errors that resulted during a given assay or assay step, or combinations thereof.

Still further, consumable data can be used as a security mechanism, e.g., to confirm that the correct assay consumable is being used in the system (referred to herein as "consumable security information"). The consumable data can include a digital signature to prove that the consumable was manufactured by the designated vendor. In one embodiment, if an inappropriate assay consumable is present in the system, e.g., a counterfeit consumable or a consumable that is otherwise incompatible with the assay system, the controller will disable the system, reader or a component thereof. In addition or alternatively, the consumable data can be used to detect the proper placement of the assay consumable in the system, e.g., the proper orientation of the assay consumable or a portion thereof, in the assay system, such that the controller will disable the system, reader or a component thereof until the assay consumable is placed in the correct orientation. Still further, the consumable data can also be used to detect a defect in the assay consumable or an assay test site and/or domain and the controller will disable the system, reader or a component thereof accordingly. For example, depending on the nature of the defect in the assay consumable or domain, the controller can disallow the use of the assay consumable in its entirety or direct the reader to disallow the use of a test site and/or domain or a set of test site and/or domain in the assay consumable. In one embodiment, the reader can perform a diagnostic analysis on the assay consumable and/or a test site and/or domain therein to identify defects therein and the controller will write the results of that diagnostic analysis to the identifier on the consumable. If the consumable is later used in a different reader, the results of this diagnostic analysis will be read by the controller and used by the reader to adjust the use of that consumable or a test site and/or domain in that consumable accordingly. In a further embodiment, the assay consumable can be subjected to a quality control process during or after its manufacture and the results of that quality control analysis can be written to the identifier for later use and/or verification by the customer of the assay consumable in an assay reader.

The consumable data can also include authorization information for consumables or test site and/or domain thereof or biological reagents, such as information regarding whether a particular customer has a valid license to use a particular consumable or biological reagent, including the number of times the customer is permitted to use the particular consumable or biological reagent in a particular assay and the limitations, if any, on that use, e.g., whether the customer's license is for research purposes only. Such information can also include validation information regarding whether a particular consumable or biological reagent has been subject to a recall or has otherwise become unsuitable or unauthorized for use. The recall information and an optional last recall check date and/or timestamp can be written to the identifier and/or provided as consumable data.

The consumable data can further include information regarding the origin of a biological reagent used in an assay consumable, test site and/or domain, including for example an identification of an original sample from which it was derived or the number of generations removed it is from an original sample. For example, if an assay reagent used in an assay is an antibody, the consumable data can include the identification of the hybridoma from which the antibody was derived, e.g., the ATCC accession number for that hybridoma.

According to various embodiments, biological samples or reagents that are provided in or with the consumables described above can be licensed separately from systems designed to operate on the biological reagents. In various embodiments the assay system, reader or a component thereof is coupled to a network that allows the system to communicate over public and/or private networks with computer systems that are operated by or on behalf of the customers, manufacturers and/or licensors of the biological reagents, consumables or systems. In various embodiments, a limited license can provide for the use of licensed biological reagents, consumables or systems for a particular biological analysis on only licensed systems. Accordingly, a system can authenticate a biological reagent, consumable or system based on, for example, a digital signature contained in the identifier associated with a particular consumable and/or provided as consumable data, if a particular customer has a valid license. In various embodiments, the identifier and/or consumable data can also be used to provide for a one time use such that biological reagents cannot be refilled for use with the same authentication.

In certain embodiments, when the identifier is read by a system, reader or component thereof that has access to a public or private data network operated by or on behalf of the customers, manufacturers and/or licensors of the biological reagents, consumables or systems, certain consumable data can be communicated to the assay system and read, written or erased locally via the identifier/controller on the assay system. For example, recall and/or license information can be a subset of consumable data that is available via a direct and/or indirect interface, whereas additional consumable data e.g., lot-specific, expiration date, calibration data, consumable specific information, assay domain information, assay results information, consumable security information, or combinations thereof, can be stored locally on the identifier and otherwise unavailable via the network connections on the assay system. In one embodiment, recall, license and/or consumable security information can be available via the network connections on the assay system and/or stored to the storage medium as consumable data and the remaining consumable data is stored locally on the identifier. The assay system or reader includes system hardware, system firmware, system data acquisition and control software, and method or consumable data. In various embodiments, the system hardware includes electronic control and data processing circuitry, such as a microprocessor or microcontroller, memory, and non-volatile storage. In various embodiments, the system hardware also includes physical devices to manipulate biological reagents such as robotics and sample pumps. In various embodiments, the system firmware includes low-level, computer-readable instructions for carrying out basic operations in connection with the system hardware. In various embodiments, the system firmware includes microprocessor instructions for initializing operations on a microprocessor in the system hardware.

The system data acquisition and control software is higher-level software that interfaces with the system firmware to control the system hardware for more specific operations such as operating a charge coupled device (CCD) to acquire visual luminescence information regarding a particular biological analysis. In various embodiments the data acquisition and control software includes a software-implemented state machine providing, for example, the following states: (i) idle; (ii) running; (iii) paused; and (iv) error. In various embodiments, when the state machine is in the idle state, it can receive an instruction from the general purpose machine to perform a particular data acquisition or system control operation. In various embodiments, the general purpose computer opens a TCP/IP socket connection to the system, determines whether the system is in the idle state and then begins transmitting instructions and/or parameters. In various embodiments, an encrypted TCP/IP connection is established, using, for example, the SSH protocol. The instructions and/or parameters can be in the form of ASCII encoded, human readable consumable and/or method information that defines the behavior of the biological system. In various embodiments, the consumables and/or methods are stored in the form of ASCII text files. In various embodiments, the general purpose computer uses the FTP protocol to transfer the ASCII text files to the system. In various other embodiments the method and/or consumable information is stored in and read from the identifier. The method and/or consumable information can be stored in the form of an ASCII text file in the identifier, but it is understood that the information can be represented in other data formats without departing from the present teachings.

According to various embodiments, the consumable, macro, and/or method information includes parameters that can be used by the system data acquisition and control software to perform specific data acquisition and system control operations. In various embodiments, the method and/or consumable information contains sequences of operations to be performed by the system or control parameters for use in connection with the data acquisition or control software.

(ii) Assay Process Information

In addition, the consumable data can include assay process information concerning the individual assay parameters that should be applied by the system or reader during the assay. For example, such consumable data can include a sequence of steps for a given assay, the identity, concentration and/or quantity of assay reagents that should be used or added during the assay or during a particular step of an assay, e.g., buffers, diluents, and/or calibrators that should be used in that assay. The consumable data can also include the type or wavelength of light that should be applied and/or measured by the system or reader during the assay or a particular step of a multi-step assay; the temperature that should be applied by the system or reader during the assay; the incubation time for an assay; and statistical or other analytical methods that should be applied by the system or reader to the raw data collected during the assay.

In one embodiment, one or more steps of an assay protocol can be tailored to an individual consumable or lot of consumables. One or more steps of a protocol can differ from consumable lot to lot and/or from individual consumable to consumable within a given lot and the consumable data stored to the system includes instructions to tailor those steps of the assay protocol. This type of consumable data can be used by the system to adjust one or more operations performed by the system before, during and/or after the conduct of an assay by the system. Moreover, this type of consumable data can optionally be adjusted by the system user at the user's discretion. For example, dilution steps in an assay protocol can be adjusted to account for lot to lot or consumable to consumable differences. The amount of diluent added and/or the nature of the diluent can be altered based on such differences. Similarly, the amount of a given reagent that can be added during the conduct of an assay, an incubation period and/or temperature for one or more steps of an assay can also be dependent on lot to lot or consumable to consumable differences. Each of these are non-limiting examples of consumable data that can be saved to the storage medium of the system.

Moreover, the consumable data comprises information that directly or indirectly controls a component of the assay system, e.g., one or more photodetectors, a light tight enclosure; mechanisms to transport the assay consumables into and out of the reader; mechanisms to align and orient the assay consumables with the one or more photodetector(s) and/or with electrical contacts in the reader; additional mechanisms and/or data storage media to track and/or identify assay consumables; one or more sources of electrical energy to induce luminescence; mechanisms to store, stack, move and/or distribute one or more consumables; mechanisms to measure light from a consumable during the assay sequentially, substantially simultaneously or simultaneously from a plurality of test sites of the consumable; or combinations thereof.

The consumable data can also include assay process information comprising assay parameters to be applied by the reader during the assay; a sequence of steps to be applied by the reader during the assay; the identity, concentration, and/or quantity of assay reagents to be used or added during the assay; the type or wavelength of light to be applied and/or measured by the reader during the assay; the temperature to be applied by the reader during the assay; an incubation time for the assay; statistical or analytical methods to be applied by the reader to raw data collected during the assay; or combinations thereof (such assay process information can optionally be adjusted by the user). In one specific embodiment, the assay conducted with the consumable is a multi-step assay and the assay process information relates to a step or step(s) of the multi-step assay. In this embodiment, the consumable/test site information comprises information concerning assays previously performed by a reader on one or more test sites of the consumable; information concerning assays to be performed by an assay reader or a component thereof on one or more test sites within the consumable; or combinations thereof.

The consumable data can additionally include information regarding a consumable, test site, domain, sector, or a biological reagent or sample as individual operations are performed on that consumable, test site, domain, sector, or biological reagent or sample, for example during manufacture of the consumable, test site, domain, sector, or biological reagent or while an assay or step is being performed on the consumable, test site, domain, sector, or biological reagent or sample. For example, if an assay consumable includes a plurality of assay test sites, domains, and/or sectors, the assay system can perform an assay or step of a multi-step assay on a single test site, domain and/or sector of the assay consumable. Once that assay or assay step is completed by the assay system, the controller records the results of that assay, e.g., the raw or analyzed data generated during the assay or assay step, to the identifier, and/or the controller records which test site, domain and/or sector of the assay consumable were used during the assay or assay step and/or which test site, domain and/or sector of the assay consumable have yet to be used. The assay consumable can be stored for later use and when the customer is ready to use another test site, domain and/or sector of the assay consumable, the controller reads the consumable data stored on the identifier of the assay consumable to identify which test site, domain and/or sector has been used, has yet to be used, and/or the results of those assays. The controller can then instruct the assay system, reader or component thereof to conduct an assay or assay step on an unused test site, domain and/or sector.

In addition, a given assay protocol can require a set of consumables of a particular type. Therefore, if the customer inputs a specific type of assay consumable, e.g., a multi-well assay plate, for use in a particular assay protocol, one or more additional assay consumables can be required to carry out that assay protocol in the system, e.g., one or more reagents can be required for use with that multi-well assay plate. Each of the required consumables can include a consumable identifier with information concerning the consumable requirements for an assay protocol. When one of the required consumables is input into the assay system and the identifier controller interacts with the consumable identifier for that consumable, the system will take an inventory of the components present in the system and compare the results to the consumable requirements stored to the consumable identifier and/or stored to the storage medium and/or provided as consumable data. If any required consumables are not present or are present in insufficient supply, the system will prompt the customer to input the additional required consumables for that assay protocol based on the information stored on the required consumable identifier. If two or more assay consumables are used in the system, the instrument will correctly identify a first assay consumable and any associated consumables based on the consumable requirements stored to the identifiers associated with each consumable. The system will verify that the assay consumable and associated consumables are loaded on the system before the sample is run. In the case where only the first assay consumable is loaded into the system without the corresponding associated consumable, the system will prompt the customer to load the associated consumable if the instrument does not identify the associated consumable within the system within a predefined period of time. The system will notify the customer if mismatched assay consumables are loaded on the instrument. The system will not run samples if there are no available matched sets of assay consumables (e.g., multi-well assay plates and given reagents for a particular assay). The system will check for assay consumable expiration prior to the start of an assay and the system will alert the customer and prevent the use of an expired consumable. The system will not process a sample if the consumables have expired prior to sample aspiration. If a partially used assay consumable is installed into a different instrument, consumable usage will automatically start with the next available unused well.

The identifier can also be used to track the time a given assay consumable is present in the assay system. Therefore, when an assay consumable is inserted into or contacted with an assay system, a timer is initiated in the assay system and the start time is recorded to the identifier. When the assay is initiated by the system on the consumable or a test site, domain and/or sector within the consumable, the time is also recorded to the identifier. If the instrument, system or a component thereof is shutdown e.g., by turning the power off), the timer is stopped and that time is recorded to the identifier. Thus, whenever the timer is stopped, the accumulated onboard time is recorded to the identifier.

(iii) Analytical Tools

In another embodiment, the consumable data further includes one or more analytical tools that can be applied by the system to analyze data generated during and/or after the conduct of an assay. In addition, such analytical tools can include instructions for the customer and/or the system to generate a specific output by the system software after the conduct of an assay, e.g., a tailored data report and/or format for the results of the analysis based on the consumable data. Alternatively or additionally, the analytical tools can further include one or more statistical algorithms that can be applied by the system to the data. For example, the consumable data can include a selection of two or more statistical algorithms that can be used to analyze data resulting from use of a given consumable and the customer can optionally select the appropriate algorithm for the desired data analysis. The consumable data can also include information that can be used by the customer to select the appropriate algorithm for his or her needs, e.g., technical notes or literature references related to algorithm selection.

Analytical tools can differ from consumable lot to lot and/or from individual consumable to consumable within a given lot. In this embodiment, the consumable data is used by the system to adjust the analytical processing tools applied by the system software in the conduct of an assay or after the assay is completed and the results are generated and/or displayed. Such analytical processing tools include but are not limited to assay thresholds and/or calibration curves that can be applied to one or more steps of an assay protocol that can also be altered based on consumable differences. In a specific embodiment, for a given consumable type and/or desired use, the consumable data can include a project management tool that schedules the conduct of one or more assays or steps thereof using a given consumable in the system or with a set of consumables. Still further, such analytical processing tools can optionally be adjusted by the system user at the user's discretion. Analytical tools can be sent to the customer via a direct or indirect interface between the system and the customer.

(iv) Assay System Maintenance Information

Consumable data can further comprise system maintenance information to the customer, including but not limited to system monitoring reports, system components usage, service history, system troubleshooting information, the results of diagnostics run on the system, control charting, periodic maintenance scheduling, warranty information regarding the system and/or a components thereof, or combinations thereof. The system software can be programmed to monitor various components of the system and automatically or when prompted, send monitoring reports to a remote computing system and/or to a service technician. If a direct interface is not enabled, the system can prompt the customer to send monitoring reports to the CD server via an indirect interface. In addition or alternatively, such system monitoring reports can be accessed by a service technician charged with the task of maintaining and/or servicing the system on site or remotely. In this embodiment, a service technician can communicate with a customer regarding service of or assistance with an instrument via a direct or indirect interface. In a specific embodiment in which a direct interface is enabled, the CD server monitors system component usage and/or warranty information and based on standard system component lifetimes and/or warranty terms, schedules periodic system/component maintenance and/or upgrades by a service technician. However, the system can be programmed to automatically monitor such information on the system and it can periodically prompt the customer to send the CD server the output of such monitoring activities via an indirect interface if a direct interface is not enabled to enable a service technician to assess the status of the system and to determine if system service or maintenance is required. In addition, the CD server can maintain a log of the service history for a given assay system and schedule a service call by a service technician (this can be done using either a direct or indirect interface). The remote computing system can also send an individual assay system software upgrades via a direct or indirect interface.

(v) System-Consumable Promotional information

In another embodiment, consumable data includes promotional materials, e.g., when a new type or lot of consumables becomes available, especially those products historically used by a given customer. Such promotional materials can also relate to new assay systems, modifications to a current system, and/or optional attachments or improvements to a current system, especially those modifications, attachments or improvements that specifically relate to a system the customer owns or operates and/or those modifications, attachments or improvements that might be of interest to the customer based on that customer's prior usage. Consumable data of this type can also include literature references, brochures, product inserts, technical and application notes, technical presentations, conference information, and promotional seminars, especially those that can relate to one or more consumables/systems used by a given customer. Such promotional information can be provided to the customer via a direct or indirect interface between the customer and vendor.

(vi) Technical Support Information

Consumable data also includes technical support information that can assist the customer in the use of a consumable or system, e.g., product insert and data sheet information, information relates to associated products intended to be used with that consumable, instructions for use, training materials, tutorials, recommended usage and/or storage information, data analysis templates, template reports, calibration curves, lot specific QC data, verified limits of quantitation, and trouble-shooting methods and/or algorithms. For consumables that include or are provided with one or more additional consumables, e.g., reagents, the consumable data can also include a reagent catalog number, reagent lot specific information, reagent manufacture dates, reagent expiration dates, instructions for use, training materials, tutorials, recommended usage and/or storage, and the like. Technical support information can also include receiving feedback or assistance via a direct or indirect interface with a technical support representative, e.g., customer training modules, consulting services, and/or live customer service assistance capabilities to facilitate the customer experience (i.e., live-chatting). It will be understood that technical support information can relate to a consumable, system, or both.

In a specific embodiment, Table 1 includes a list of consumable data that can be stored to a consumable identifier and/or exchanged between a CD server and a system via a direct or indirect interface.

TABLE 1

| Types of Consumable Data | Examples of Consumable Data |
|---|---|
| Consumable identification and/or configuration information | Consumable type<br>Consumable description/configuration<br>Consumable lot number<br>Consumable expiration date<br>Certificate of analysis<br>Lot specific quality control data<br>Catalog number<br>Associated consumables<br>Verified limits of quantitation<br>shipping manifest for complete order<br>recommended storage conditions<br>product insert<br>chain of custody information |
| Assay protocol steps | Instructions for use in the system |
| Analytical tools that can be applied by the system | Data analysis templates<br>Report templates<br>Calibration curves<br>Statistical analyses that can be applied to a data set<br>Assay thresholds<br>Project management scheduler |
| Assay system maintenance information | Preventative maintenance tips & reminders for system or components thereof<br>Service reminders & scheduling for service visits<br>Warranty information for system or components thereof<br>System software upgrades/patches<br>Service history information<br>Individual system component monitoring and remote maintenance |

TABLE 1-continued

| Types of Consumable Data | Examples of Consumable Data |
|---|---|
| System-consumable promotional information System and/or consumable technical support information | New consumable and/or system offerings Literature references that relate to customer-system use Product insert Training materials Access to customer support representatives Usage recommendations, e.g., sample type and sample preparation procedures Recommended usage configuration Trouble shooting algorithms Concentration ranges for controls Expected calibration curve data for consumable Recommended calibration curve concentrations for consumable |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications, including U.S. application Ser. No. 12/844,345, filed Jul. 27, 2010, are cited herein, the disclosures of which are incorporated by reference in their entireties.

What is claimed is:

1. A non-transitory computer readable medium having stored thereon a computer program which, when executed by a computer system, causes the computer system to perform a method of generating and maintaining consumable data and consumable data for a consumable comprising:
   (a) generating a database comprising consumable data associated with said consumable, wherein said database comprises information used to associate said consumable data with said consumable;
   (b) maintaining said database on a server; and
   (c) automatically adjusting an assay system based on said consumable data of said consumable or automatically, directly or indirectly, controlling a component of said assay system via said consumable data, wherein said adjusting is at least one of: adjusting dilution steps in an assay protocol to account for lot to lot or consumable to consumable differences; adjusting the amount of diluent added and/or the nature of the diluent to account for lot to lot or consumable to consumable differences; adjusting the amount of a given reagent that can be added during the conduct of an assay to account for lot to lot or consumable to consumable differences; adjusting an incubation period and/or temperature for one or more steps of an assay to account for lot to lot or consumable to consumable differences.

2. The non-transitory computer readable medium of claim 1 wherein said server comprises a master repository including a directory comprising a master consumable data directory, a master system identifier directory, a customer data directory, or combinations thereof.

3. The non-transitory computer readable medium of claim 2 wherein said master repository comprises a master consumable data directory and an interface to one or more supplemental vendor directories comprising a master system identifier directory, a customer data directory, or combinations thereof.

4. The non-transitory computer readable medium of claim 1, wherein step (c) further comprises automatically adjusting the assay system based on said consumable data of said consumable, and said automatic adjustment is one of (i) enabling full access to the assay system; (ii) enabling partial access to the assay system; and (iii) denying access to the assay system.

5. The non-transitory computer readable medium of claim 1, wherein the program further comprises the step of:
   maintaining said database on a server, wherein said consumable data is selected from the group consisting of, consumable identification and configuration information, lot identification information, assay sample information, chain of custody information.

6. The non-transitory computer readable medium of claim 5, wherein said server comprises a master repository including a directory comprising a master consumable data directory, a master system identifier directory, a customer data directory, or combinations thereof.

7. The non-transitory computer readable medium of claim 1, wherein the database further comprises order fulfillment information, said order fulfillment information comprising information of components of an order of consumables.

8. The non-transitory computer readable medium of claim 7, wherein the program is further configured to verify that all components of the order have been supplied to a customer.

9. The non-transitory computer readable medium of claim 1, wherein the assay system is adapted to review local consumable data stored on a storage medium to identify the local consumable data that can be used for the conduct of an assay using a particular consumable and wherein if the storage medium includes the identified local consumable data, the particular consumables can be used in the assay system, and wherein if the storage medium does not include the local consumable data for the particular consumable, the assay system queries a customer for the consumable data and the customer communicates with a vendor to receive the requisite local consumable data such that the particular consumable can be used by the assay system.

10. A computer implemented method of generating and maintaining consumable data and consumable data for a consumable comprising:
   (a) generating a database comprising consumable data associated with said consumable, wherein said database comprises information used to associate said consumable data with said consumable; and
   (b) maintaining said database on a server; and
   (c) automatically adjusting an assay system based on said consumable data of said consumable or automatically, directly or indirectly, controlling a component of said assay system via said consumable data, wherein said adjusting is at least one of adjusting dilution steps in an assay protocol to account for lot to lot or consumable to consumable differences; adjusting the amount of diluent added and/or the nature of the diluent to account for lot to lot or consumable to consumable differences; adjusting the amount of a given reagent that can be added during the conduct of an assay to account for lot to lot or consumable to consumable differences; adjusting an incubation period and/or temperature for one or more steps of an assay to account for lot to lot or consumable to consumable differences.

11. The computer implemented method of claim 10, wherein step (c) further comprises automatically adjusting the assay system based on said consumable data of said consumable, and said automatic adjustment is one of (i) enabling full access to the assay system; (ii) enabling partial access to the assay system; and (iii) denying access to the assay system.

12. The computer implemented method of claim 10, wherein the method further comprises the step of:
maintaining said database on a server, wherein said consumable data is selected from the group consisting of, consumable identification and configuration information, lot identification information, assay sample information, chain of custody information.

13. The computer implemented method of claim 12, wherein said server comprises a master repository including a directory comprising a master consumable data directory, a master system identifier directory, a customer data directory, or combinations thereof.

14. The computer implemented method of claim 10, wherein the database further comprises order fulfillment information, said order fulfillment information comprising information of components of an order of consumables.

15. The computer implemented method of claim 14, wherein the method further comprises a step of verifying that all components of the order have been supplied to a customer.

16. The computer implemented method of claim 10 wherein said server comprises a master repository including a directory comprising a master consumable data directory, a master system identifier directory, a customer data directory, or combinations thereof.

17. The computer implemented method of claim 16 wherein said master repository comprises a master consumable data directory and an interface to one or more supplemental vendor directories comprising a master system identifier directory, a customer data directory, or combinations thereof.

18. The computer implemented method of claim 10, wherein the assay system is adapted to review local consumable data stored on a storage medium to identify the local consumable data that can be used for the conduct of an assay using a particular consumable and wherein if the storage medium includes the identified local consumable data, the particular consumables can be used in the assay system, and wherein if the storage medium does not include the local consumable data for the particular consumable, the assay system queries a customer for the consumable data and the customer communicates with a vendor to receive the requisite local consumable data such that the particular consumable can be used by the assay system.

19. A non-transitory computer readable medium having stored thereon a computer program which, when executed by a computer system, in combination with a remote computing system, causes the computer system to perform a method of generating and maintaining consumable data and consumable data for a consumable comprising:

(a) manufacturing said consumable used in the conduct of an assay by an assay system;
(b) generating a database comprising consumable data associated with said consumable, wherein said database comprises information used to associate said consumable data with said consumable; and
(c) maintaining said database on a server,
said remote computing system being adapted to control customer access to said assay system by a system vendor wherein said system comprises a s stem identifier, said remote computing system being adapted to perform the following operations:
(aa) receiving said system identifier from a customer, wherein said system identifier is sent to a vendor computing system;
(bb) identifying said system identifier by said vendor; and
(cc) performing one or more operations selected from:
(I) enabling full access to said assay system and/or a consumable used in said assay system;
(II) enabling partial access to said assay system and/or a consumable used in said assay system; or
(III) denying access to said assay system and/or a consumable used in said assay system.

20. The non-transitory computer readable medium of claim 19 further comprising the step of automatically adjusting the assay system based on said consumable data of said consumable, wherein said automatic adjustment is one of (i) enabling full access to the assay system; (ii) enabling partial access to the assay system; and (iii) denying access to the assay system.

21. The non-transitory computer readable medium of claim 19, wherein said consumable data comprises an identifier, wherein the identifier comprises information of how the consumable is manufactured.

22. The non-transitory computer readable medium of claim 21, wherein the identifier is programmed during step (a).

23. The non-transitory computer readable medium of claim 19, wherein said consumable data is generated by a consumable vendor.

24. The non-transitory computer readable medium of claim 19, wherein said consumable data is selected from the group consisting of, consumable identification and configuration information, lot identification information, assay sample information, chain of custody information.

25. The non-transitory computer readable medium of claim 24, wherein said server comprises a master repository including a directory comprising a master consumable data directory, a master system identifier directory, a customer data directory, or combinations thereof.

26. The non-transitory computer readable medium of claim 25, wherein the master repository comprises a directory for each consumable manufactured in step (a).

27. The non-transitory computer readable medium of claim 19, wherein the database further comprises order fulfillment information, said order fulfillment information comprising information of components of an order of consumables.

28. The non-transitory computer readable medium of claim 27, wherein the program is further configured to verify that all components of the order have been supplied to a customer.

29. The non-transitory computer readable medium of claim 19, wherein the assay system is adapted to review local consumable data stored on a storage medium to identify the local consumable data that can be used for the conduct of an assay using a particular consumable and wherein if the storage medium includes the identified local consumable data, the particular consumables can be used in the assay system, and wherein if the storage medium does not include the local consumable data for the particular consumable, the assay system queries a customer for the consumable data and the customer communicates with a vendor to receive the requisite local consumable data such that the particular consumable can be used by the assay system.

30. A computer implemented method of generating and maintaining consumable data and consumable data in combination with a remote computing system for a consumable comprising:
(a) manufacturing said consumable used in the conduct of an assay by an assay system;
(b) generating a database comprising consumable data associated with said consumable, wherein said database comprises information used to associate said consumable data with said consumable; and
(c) maintaining said database on a server,
said remote computing system being adapted to control customer access to said assay system by a system vendor wherein said system comprises a system identifier, said remote computing system being adapted to perform the following operations:
(aa) receiving said system identifier from a customer, wherein said system is sent to a vendor computing system;
(bb) identifying said system identifier by said vendor; and
(cc) performing one or more operations selected from:
(I) enabling full access to said assay system and/or a consumable used in said assay system;
(II) enabling partial access to said assay system and/or a consumable used in said assay system; or
(III) denying access to said assay system and/or a consumable used in said assay system.

31. The computer implemented method of claim 30 further comprising the step of automatically adjusting the assay system based on said consumable data of said consumable, wherein said automatic adjustment is one of (i) enabling full access to the assay system; (ii) enabling partial access to the assay system; and (iii) denying access to the assay system.

32. The computer implemented method of claim 30; wherein said consumable data comprises an identifier, wherein the identifier comprises information of how the consumable is manufactured.

33. The computer implemented method of claim 32, wherein the identifier is programmed during step (a).

34. The computer implemented method of claim 30, wherein said consumable data is generated by a consumable vendor.

35. The computer implemented method of claim 30, wherein said consumable data is selected from the group consisting of consumable identification and configuration information, lot identification information, assay sample information, chain of custody information.

36. The computer implemented method of claim 35, wherein said server comprises a master repository including a directory comprising a master consumable data directory, a master system identifier directory, a customer data directory, or combinations thereof.

37. The computer implemented method of claim 36, wherein the master repository comprises a directory for each consumable manufactured in step (a).

38. The computer implemented method of claim 30, wherein the database further comprises order fulfillment information, said order fulfillment information comprising information of components of an order of consumables.

39. The computer implemented method of claim 38, wherein the method further comprises verifying that all components of the order have been supplied to a customer.

40. The computer implemented method of claim 30, wherein the assay system is adapted to review local consumable data stored on a storage medium to identify the local consumable data that can be used for the conduct of an assay using a particular consumable and wherein if the storage medium includes the identified local consumable data, the particular consumables can be used in the assay system, and wherein if the storage medium does not include the local consumable data for the particular consumable, the assay system queries a customer for the consumable data and the customer communicates with a vendor to receive the requisite local consumable data such that the particular consumable can be used by the assay system.

* * * * *